United States Patent [19]
Palsson et al.

[11] Patent Number: 5,459,069
[45] Date of Patent: Oct. 17, 1995

[54] DEVICE FOR MAINTAINING AND GROWING HUMAN STEM AND/OR HEMATOPOIETICS CELLS

[75] Inventors: Bernhard O. Palsson; Stephen G. Emerson; Richard M. Schwartz, all of Ann Arbor, Mich.

[73] Assignee: The Regents of the University of Michigan, Ann Arbor, Mich.

[21] Appl. No.: 178,433

[22] Filed: Jan. 6, 1994

Related U.S. Application Data

[63] Continuation of Ser. No. 845,969, Mar. 4, 1992, abandoned, which is a continuation-in-part of Ser. No. 366,639, Jun. 15, 1989, abandoned.

[51] Int. Cl.$^6$ ............................. C12M 3/00; C12M 3/04
[52] U.S. Cl. ...................... 435/289.1; 435/293.1; 435/293.2; 435/297.1; 435/297.2
[58] Field of Search ............... 435/240.24, 240.243, 435/284–286, 296–298, 310, 311, 803, 808, 809, 813, 313, 818; 356/38, 436, 440, 441, 442, 244, 246; 73/54.37, 54.39, 150 A; 422/48

[56] References Cited

U.S. PATENT DOCUMENTS

| | | | |
|---|---|---|---|
| 4,225,671 | 9/1980 | Puchinger et al. | 435/285 |
| 4,435,508 | 3/1984 | Gabridge | 435/284 |
| 4,537,860 | 8/1985 | Tolbert et al. | 435/284 |
| 4,721,096 | 1/1988 | Naughton et al. | |
| 4,748,124 | 5/1988 | Vogler. | |
| 4,810,643 | 3/1989 | Souza. | |
| 4,831,869 | 5/1989 | Fowler et al. | 73/150 A |
| 4,833,083 | 5/1989 | Saxena. | |
| 4,839,292 | 6/1989 | Cremonese | 435/313 |
| 4,874,201 | 7/1989 | Kaswasaki et al. | |
| 4,894,342 | 1/1990 | Guinn et al. | 435/284 |
| 4,908,319 | 3/1990 | Smyczek et al. | 435/285 |
| 4,948,728 | 8/1990 | Stephanopoulos et al. | |
| 5,010,014 | 4/1991 | Gebhardt | 435/310 |
| 5,028,541 | 7/1991 | Kiel et al. | 435/286 |
| 5,032,508 | 7/1991 | Naughton et al. | |
| 5,135,853 | 8/1992 | Dziewulski et al. | 435/284 |

FOREIGN PATENT DOCUMENTS 0155237  9/1985  European Pat. Off..

OTHER PUBLICATIONS

Cell, vol. 47, pp. 3–10, Oct. 10, 1986, Yu–Chung Yang, et al., "Human IL–3 (Multi–CSF): Identification by Expression Cloning of a Novel Hematopoietic Growth Factor Related to Murine IL–3".

Canadian Journal of Chemical Engineering, vol. 64, Aug. 1986, S. R. Adamson, et al., "Industrial Mammalian Cell Culture", pp. 531–539.

Aiken et al., *J. of Pediatric Surgery*, vol. 25, No. 1, pp. 140–145, 1990.

Al–Lebban et al., *Exp. Hematol*, vol. 18, pp. 180–184, 1990.

Baines et al., *Exp. Hematol*, vol. 16, pp. 785–789, 1988.

Batt et al., *Biotechnol. Prog.* vo.. 6, pp. 458–464, 1990.

Bodine et al., *Proc. Natl. Acad. Sci. USA*, vol. 86, pp. 8897–8901, 1989.

Borinaga et al., *British Journal of Haematology*, vol. 76, pp. 476–483, 1990.

(List continued on next page.)

*Primary Examiner*—William H. Beisner
*Attorney, Agent, or Firm*—Oblon, Spivak, McClelland, Maier, & Neustadt

[57] ABSTRACT

Devices are provided for the growth of human stem and/or hematopoietic cells in culture. Bioreactors are provided in which diverse cell types are simultaneously-cultured in the presence of appropriate levels of nutrients and growth factors substantially continuously maintained in the bioreactor while removing undesirable metabolic products. This simultaneous culture of multiple cell types successfully reconstructs hematopoietic tissue ex vivo. Optionally, at least one growth factor is provided through excretion by transfected stromal cells, particularly heterologous cells. The stromal cells and hematopoietic cells are maintained separately and both the adherent and non-adherent cells are harvested.

10 Claims, 14 Drawing Sheets

OTHER PUBLICATIONS

John Brandt et al., Detection of a Human Hematopoietic Progenitor Cell Capable of Forming Blast Cell Containing Colonies In Vitro, *J. Clinical Invest.* (1988), pp. 165–173.

Caldwell et al., *Biotechnology Progress,* vol. 7, No. 1, pp. 1–8, 1991.

Caldwell et al., *J. of Cellular Physiology,* vol. 147, pp. 344–353, 1991.

Coutinho et al., *Blood,* vol. 75, No. 11, pp. 2118–2129, 1990.

Dexter et al., in *Long–Term Bone Marrow Culture,* pp. 57–96, Alan Liss, New York, 1984.

Donahue et al., *Science,* vol. 241, 1820–1823, 1988.

Ehrlich et al., *In Vitro,* vol. 14, No. 5 pp. 443–450, 1978.

Favre et al., *Blood,* vol. 75, No. 1, pp. 67–73, 1990.

Feder, *Scientific American,* vol. 248, No. 1, pp. 36–43, Jan. 1983.

Gabrilove et al., *Proc. Natl. Acad. Sci. USA,* vol. 83, pp. 2478–2482, Apr. 1986.

Greenberger, in *Hematopoiesis,* (Golde, Ed.), pp. 203–243, 1984.

Heyworth et al., *Growth Factors,* vol. 2, pp. 197–211, 1990.

Hubbell et al., *Biotechnology,* vol. 9, pp. 568–572, Jun. 1991.

Hughes et al., *Blood,* vol. 74, No. 6, pp. 1915–1922, Nov. 1, 1989.

Krumwieh et al., *International Journal of Cell Cloning,* vol. 8, pp. 229–248, 1990.

Krumwieh et al., *Behring Inst. Mitt,* No. 83, pp. 250–257, 1988.

Lu et al., *British Journal or Haematology,* vol. 70, pp. 149–156, 1988.

McNiece et al., *Blood,* vol. 73, No. 4, pp. 919–923, 1989.

Migliaccio et al., *Blood,* vol. 72, No. 1, pp. 248–256, 1988.

Morioka et al., *Purification of a Granulocyte Colony–Stimulating Factor . . . ,* Res. Exp. Med., vol. 190, pp. 229–238, 1990.

Mueller, Angelika, *Folia Hematol, Leipzig,* vol. 116, No. 5, pp. 731–743, 1989.

Myers et al., *Blood,* vol. 64, No. 1, pp. 152–155, Jul. 1984.

Nolta et al., *Human Gene Therapy,* vol. 1, pp. 257–268, 1990.

Makio Ogawa, MD, PhD., *Hematology/Oncology Clinics of North America,* vol. 3, No. 3, pp. 453–465, 1989.

Parsons et al., *Journal of Pharmacological Methods,* vol. 8, pp. 73–89, 1982.

Maria Podolak–Dawidziak, *Haematologia,* vol. 23, pp. 121–123, 1990.

*Extended Abstracts,* Nov. 17–22, 259e, 1991.

Schneider et al., *Journal of Immunological Methods,* vol. 129, pp. 251–268, 1990.

Schwartz et al., *Blood,* vol. 78, No. 12, pp. 3155–3161, 1991.

Schwartz et al., *Proc. Natl. Acad. Sci. USA,* vol. 88, pp. 6760–6764, Aug. 1991.

Saeland et al., *Blood,* vol. 73, No. 5, pp. 1195–1201, 1989.

Takaue et al., *Blood,* vol. 76, No. 2, pp. 330–335, 1990.

Takaue et al., *Blood,* vol. 70, No. 5, pp. 1611–1618, Nov. 1987.

Varma et al., *Exp. Hematol.,* vol. 20, pp. 87–91, 1992.

Ventra et al., *Exp. Hematol,* vol. 18, pp. 878–882, 1990.

Lemischka, *Cell,* vol. 45, pp. 917–927 (1986).

Greaves, *Cell,* vol. 56, pp. 979–986 (1989).

Crouch et al. "The Adhesion of Animal Cells to Surfaces:" J. Chem. Tech. Biotechnol. vol. 35B (1985) pp. 273–281.

Fowler et al. "A method for Evaluating the adhesion of cells to Surfaces" British Pharmaceutical Conf. (1979).

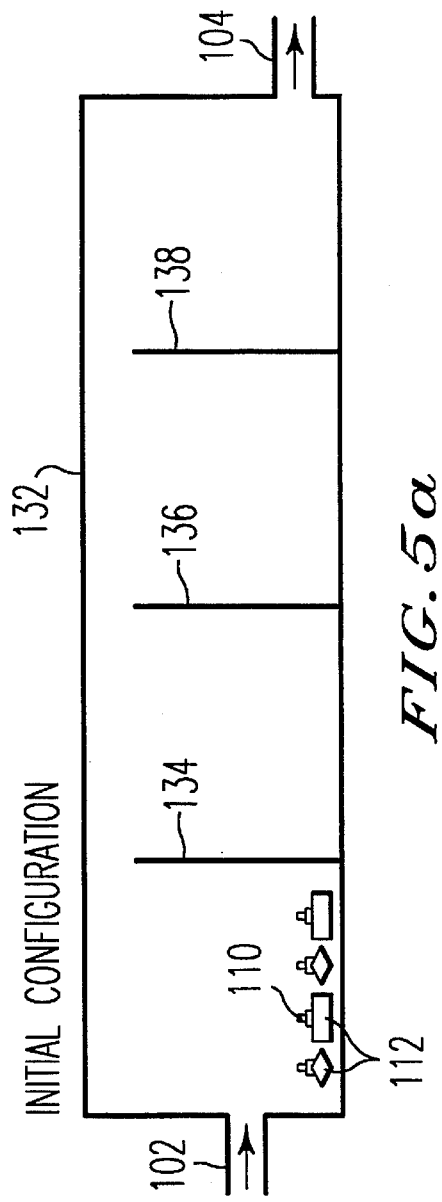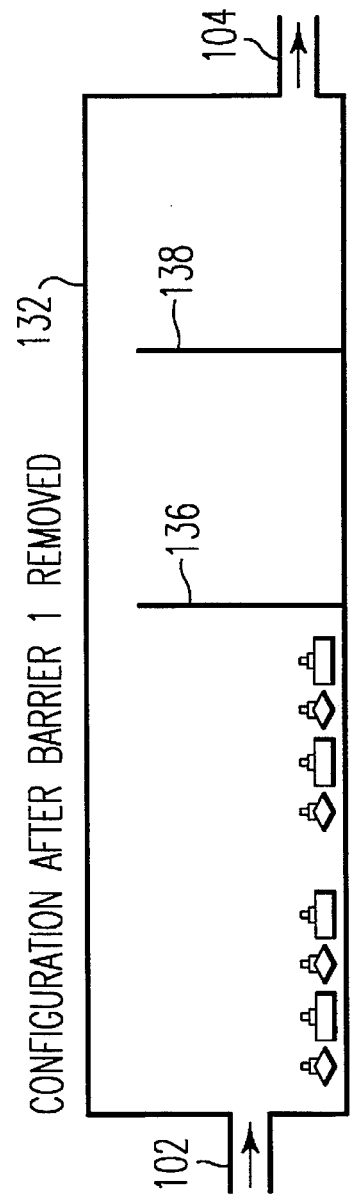

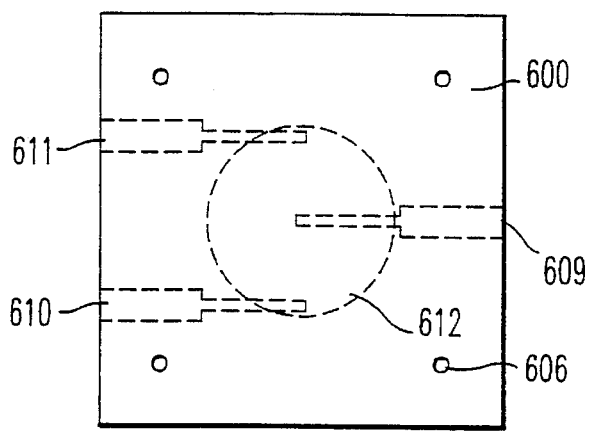 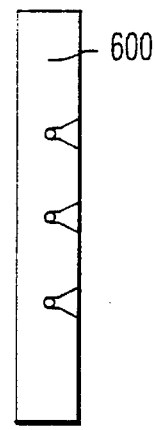
*FIG. 6a*  *FIG. 6b*
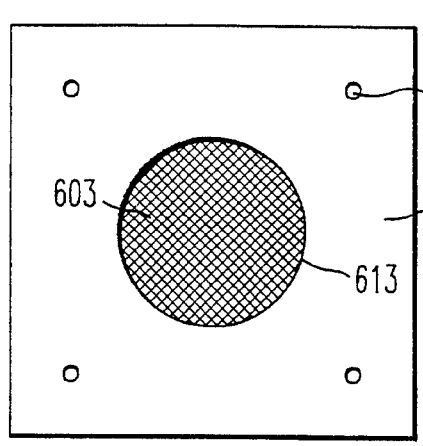 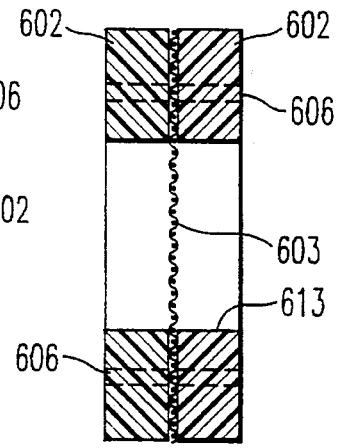
*FIG. 6c'*  *FIG. 6c''*
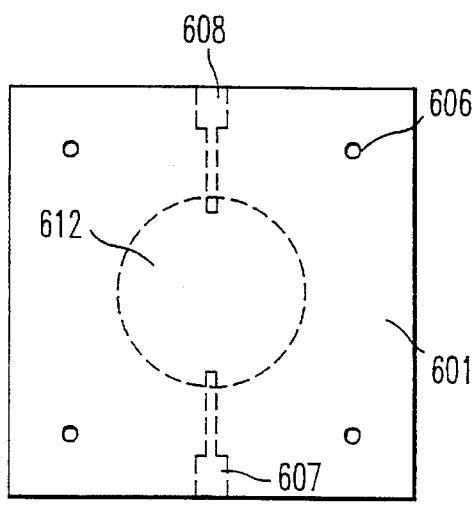 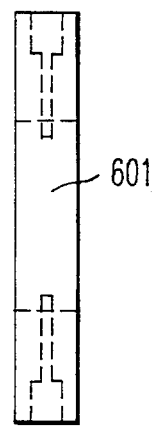
*FIG. 6d*  *FIG. 6e*

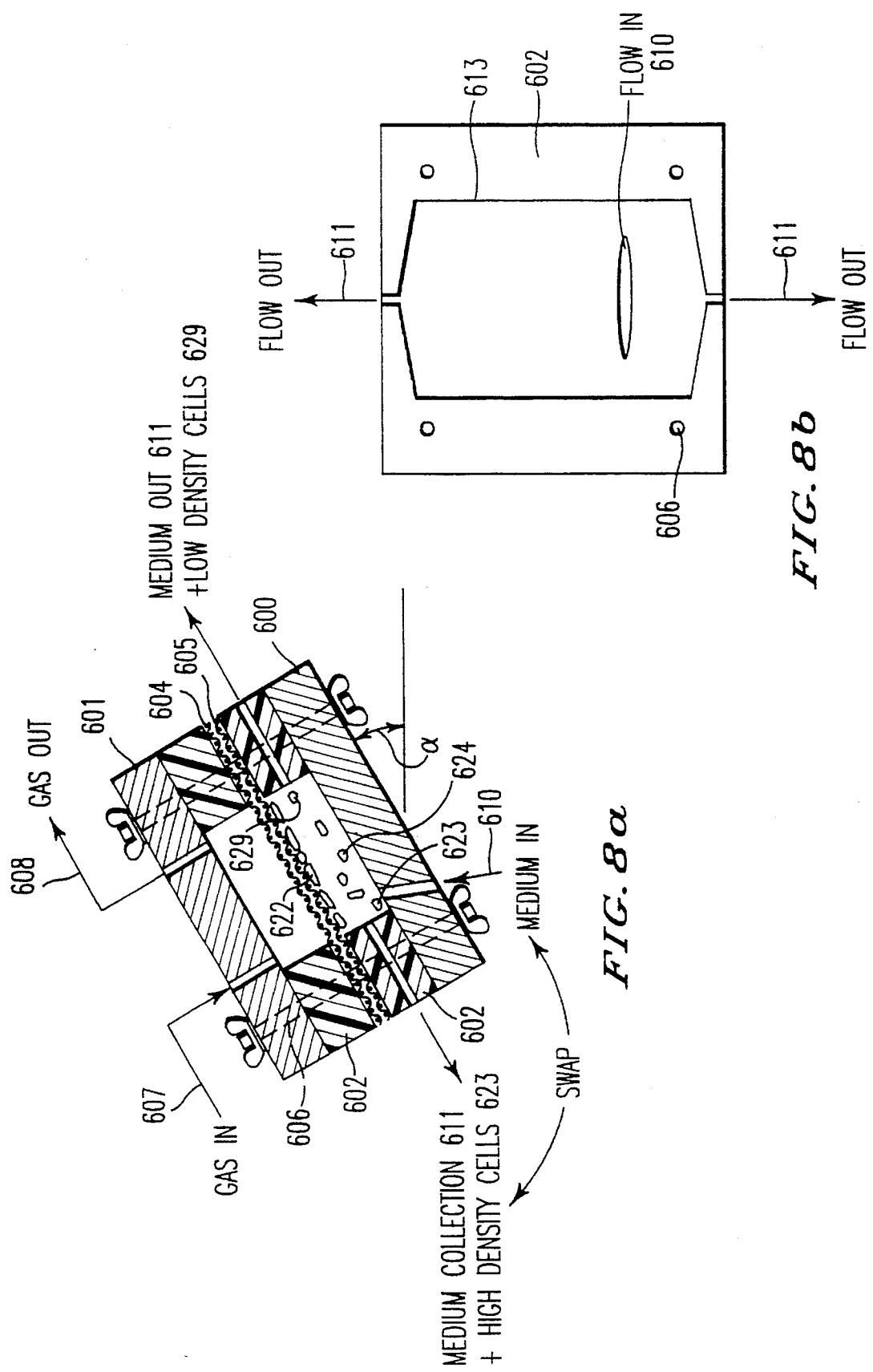

DEVICE FOR MAINTAINING AND GROWING HUMAN STEM AND/OR HEMATOPOIETICS CELLS

CROSS-REFERENCE TO RELATED APPLICATIONS

This application is a Continuation of application Ser. No. 07/845,969, filed on Mar. 4, 1992, now abandoned, which is a continuation-in-part of Ser. No. 07/366,639, filed on Jun. 15, 1989, now abandoned.

BACKGROUND OF THE INVENTION

1. Field of the Invention

The field of the invention is methods and devices for the growth of normal mammalian cells in culture, including the maintenance and selective growth of human stem and/or hematopoietic cells.

2. Discussion of the Background

There is significant interest in the ability to use cells for a wide variety of therapeutic purposes. The hematopoietic system exemplifies the extraordinary range of cells involved in protection of mammalian hosts from pathogens, toxins, neoplastic cells, and other diseases. The hematopoietic system is believed to evolve from a single stem cell, from which all the lineages of the hematopoietic system derive. The particular manner in which the stem cell proliferates and differentiates to become determined in its lineage is not completely understood, nor are the factors defined. However, once the stem cell has become dedicated to a particular lineage, there appear to be a number of factors, for example colony stimulating factors, which allow, and may direct the stem cell to a particular mature cell lineage.

There are many uses for blood cells. Platelets find use in protection against hemorrhagings an well an a source of platelet derived growth factor. Red blood cells can find use in transfusions to support the transport of oxygen. Specific lymphocytes may find application in the treatment of various diseases, where the lymphocyte is specifically sensitized to an epitome of an antigen. Stem cells may be used for genetic therapy as well as for rescue from high dose cancer chemotherapy. These and many other purposes may be contemplated.

In order to provide these cells, it will be necessary to provide a means, whereby cells can be grown in culture and result in the desired mature cell, either prior to or after administration to a mammalian host. The hematopoietic cells are known to grow and mature to varying degrees in bone, as part of the bone marrow. It therefore becomes of interest to recreate a system which provides substantially the same environment as is encountered in the bone marrow, as well as being able to direct these cells which are grown in culture to a specific lineage.

In this vein, U.S. Pat. No. 4,721,096 describes a 3-dimensional system involving stromal cells for the growth of hematopoietic cells. See also the references cited therein. Glanville et al., *Nature* (1981) 292: 267–269, describe the mouse metallothionein-I gene. Wong et al., *Science* (1985) 228: 810–815, describe human GM-CSF. Lemischka et al., *Cell* (1986) 45: 917–927, describe retrovirus-mediated gene transfer as a marker for hematopoietic stem cells and the tracking of the fate of these cells after transplantation. Yang et al., *Cell* (1986) 47: 3–10, describe human IL-3. Chen et al, Okayama, *Mol. Cell. Biol.* (1987) 7: 2745–2752, describe transformation of mammalian cells by plasmid DNA. Greaves et al., *Cell* (1989) 56: 979–986, describe the human CD2 gene. Civin et al, *J. Immunol.* (1984) 133: 1576–165, describe the CD34 antigen. Martin et al., *Cell* (1990) 63: 203211, describe human S-CSF. Forrester et al, *J. Cell Science,* (1984) 70: 93–110, discuss a parallel flow chamber. Coulombel et al., *J. Clin. Invest.,* (1986) 75: 961, describe the loss of CML cells in static cultures.

Tissue Engineering is a new and growing part of biotechnology. Its goal is to reconstitute fully or partially functioning human tissue in vitro to enable a variety of clinical and other applications. Several studies have been carried out recently that are aimed at reconstituting functioning human tissues in vitro. To date, perhaps the cultivation of human skin has been most successful.

The development of prolific in vitro human bone marrow systems has been long desired since such systems would enable a broad range of clinical, as well as scientific, applications. Such applications include:

(1) study of the basic dynamics of hematopoietic differentiation, (2) improved autologous and allogeneic bone marrow transplantation, (3) depletion of undesirable cells upon bone marrow transplantation, such as T-cells or any malignant cells, (4) gene therapy of the blood cell system, and (5) the large-scale production of mature blood cells, such as red cells and platelets.

Although long-term human bone marrow cultures (LTH-BMCs) developed in the late 1970s and early 1980s were initially disappointing in their longevity and cell productivity (see Greenberger (1984) "Long-term Hematopoietic Cultures," pp. 203–242 in "Hematopoiesis", D. W. Golde, Editor, Churchill-Livingstone, N.Y.), recent advances have markedly improved their performance. However, these improvements are carried out with a sub-clinical number of bone marrow cells in standard laboratory size tissue culture hardware. Therefore, a compelling and profound need exists for providing methods, compositions and devices that can carry a clinically meaningful number of human bone marrow cells to enable the therapies and applications described above.

These recent improvements in LTHBMC performance have used in vivo simulation in an attempt to create culture conditions that are conducive to in vitro reconstitution of hematopoietic function. A series of studies have demonstrated that this approach is successful. The function of the supporting stromal cell layer (mostly fibroblast, with some adipocytes and endothelial cells) has been shown to be significantly influenced by the medium perfusion rate, or the medium exchange schedule. Metabolic function, growth, and perhaps most importantly growth factor secretion have all been shown to be influenced by the medium exchange rate for normal human bone marrow fibroblasts (Caldwell et al, *J. Cell. Physiol.,* (1990) 147: 344–353), and even for transfected NIH-3T3 murine cells (Caldwell et al, *Biotech. Prog.,* (1991) 7: 1–8).

The ability of stroma to support human hematopoiesis in vitro has been demonstrated by the inventors to be enhanced by rapid medium exchange. See Schwartz et al, *Proc. Nat. Acad. Sci. (USA),* (1991), 88: 6760–6764 or U.S. patent application Ser. No. 07/737,024, filed Jul. 29, 1991, now abandoned. Under rapid medium exchange and at high cell densities, LTHBMCs can support the stable production of progenitor cells up to 20 weeks in culture and prolong granulopoiesis up to 19 weeks. The former result is notable in that it shows that these culture conditions can provide conditions suitable for stem cell maintenance and proliferation in vitro for extended periods of time.

Judicious use of added soluble growth factors can further improve the performance of these cultures. Some hematopoietic growth factors, such as Interleukin-3 (IL-3) and Granulocyte-Macrophage Colony-Stimulating Factor (GM-CSF), are believed to stimulate the differentiation of early hematopoietic cells. Other growth factors, such as Erythropoietin (Epo), are believed to be terminal differentiation factors that stimulate the production of mature cells of a particular lineage. It has been observed that the addition of soluble IL-3, GM-CSF and Epo in rapidly perfused human bone marrow cultures can significantly stimulate the production of mature and progenitor cells for periods of up to 6–8 weeks. During this period the cell culture regeneration rate (the time it takes to produce as many non-adherent cells as initially seeded) is about 2 weeks (for comparison, the estimated in vivo rate is about 2 days) and erythropoiesis is observed throughout the 20 week culture period. Both results are remarkable since all previous attempts to expand human bone marrow in vitro have proved unsuccessful and erythropoiesis is short lived in traditional LTHBMCs (lasting less than 2 weeks).

Thus, adjustment of culture conditions to simulate the in vivo condition more closely has dramatically improved the progenitor and non-adherent cell productivity of LTHBMCs. Further, these conditions lead to the reconstitution of blood cell lineages other than the macrophagic lineage which has been observed to dominate the composition of the non-adherent cell population in LTHBMCs and bone marrow cultures from other animal species (see review in R. M. Schwartz, "Optimization of Long-Term Bone Marrow Cultures," PhD thesis, 1991, University of Michigan). Further supplementation of the medium with the stem-cell factor (SCF, also known as the c-kit ligand of the mast cell growth factor) and interleukins 1 and 6 lead to even greater expansion in cell numbers. To date, this composition has not been publicly disclosed.

The discovery of prolific conditions for long-term maintenance and proliferation of early human hematopoietic cells in vitro in small scale standard cell culture laboratory hardware is clearly important. Even more important is the development of methods, devices and compositions that allow for the maintenance and proliferation of these cells in clinically meaningful numbers so that the important therapeutic applications, described above, can be carried out.

Bioreactor designs, which address the question of harvesting cells produced in the bioreactor, have been proposed. Interestingly, these proposed designs provide only for batch-wise harvesting of the cells by opening the reactor once a sufficient number of cells is obtained, thereby stopping the culture. For example, U.S. Pat. No. 5,010,014 describes a cell culture chamber unit comprising a cell culture region and a gas region separated by a gas-permeable wall which permits batch-wise cellular harvesting. U.S. Pat. No. 4,839,292 describes a cell culture flask which comprises two chambers separated by a gas permeable membrane. Each chamber is described as being equipped with both inlet and outlet means, and the flask is described as being suitable for batch-wise harvesting of the cells by removal of the gas permeable membrane from the reactor.

U.S. Pat. No. 4,948,728 describes a bioreactor and the use of a membrane comprised of a ceramic layer and a hydrophobic layer, with a biofilm attached to the ceramic film. This patent however does not address the question of cell harvesting.

Further, there is a need for a bioreactor permitting the maintenance of a balanced (in terms of cell type) complex primary cell culture. Human stem or hematopoietic cell cultures are very sensitive to their dynamic (i.e., rates of gas/nutrients/growth factor supply and removal) and chemical environment. Today no bioreactor design satisfactorily permits such maintenance of a balanced complex primary cell culture.

Available designs accordingly do not provide a method for harvesting cells without disrupting the culture or the maintenance of a balanced complex primary cell culture, much less both. A suitable design is thus needed permitting the maintenance and proliferation of human stem cells and/or early human hematopoietic cells in vitro, and advantageously further permitting harvesting cells produced in the reactor without disrupting the culture. There is a strongly felt need for such a design.

SUMMARY OF THE INVENTION

Accordingly objects of this invention include providing bioreactor designs which provide for the maintenance and proliferation of human stem cells and/or early human hematopoietic cells, including complex primary cell cultures, where the reactor permits harvesting of the cells produced in the bioreactor without disrupting the culture. The inventors have now discovered designs which satisfy the above objects of the invention and other objects which will become apparent from the description of the invention given hereinbelow.

Methods are provided employing reactors and compositions which allow for the efficient proliferation of human stem cells and/or hematopoietic cells in culture, particularly cells at an early stage of maturation, including human stem cells. The methods optionally employ stromal cells, normally transformed, which provide constitutive or inducible production of growth factors, which cells are physically separated to allow for easy separation of hematopoietic cells. By providing for continuous perfusion, and removing or recycling of cells as appropriate, the inventors discovered that ex vivo human stem cell division is obtained and that high densities and yields of viable hematopoietic cells may be achieved. The reactor optionally employs a protein surface for the stromal cells and either the surface or other barrier for maintaining separation of stromal cells and hematopoietic cells.

Methods are also provided employing bioreactors, methods and compositions which allow for maintenance, efficient proliferation and lineage control of human stem cells and/or hematopoietic cells in vitro. The efficient proliferation applies especially to hematopoietic cells at an early stage of maturation, including toti- and pluri-potent hematopoietic human stem cells. The methods allow for conditions that in part simulate the in vivo conditions and in part allow for specific alterations that enable the important clinical applications outlined above. The bioreactors of the invention permit continuously, periodically, or intermittently harvesting cells therefrom without disrupting the cell culture. The cells are harvested periodically when harvest cycles are determined a priori. They are harvested intermittently when harvested in resonse to an on-line measurement of the culture.

BRIEF DESCRIPTION OF THE FIGURES

FIG. 3b is a side view of the flow chamber of FIG. 3a;

FIGS. 5a and 5b are views of a flow chamber in which barriers are removed sequentially allowing the continued growth of stromal cells;

FIGS. 6a–6i are schematics showing the principal components of flat-bed hematopoietic bioreactors of the invention;

FIGS. 8a and 8b are schematics showing the principal components of flat-bed hematopoietic bioreactors with an inclined section for continuous or periodic cell harvesting, including selective cell harvesting;

DESCRIPTION OF THE SPECIFIC EMBODIMENTS

Figure 1:
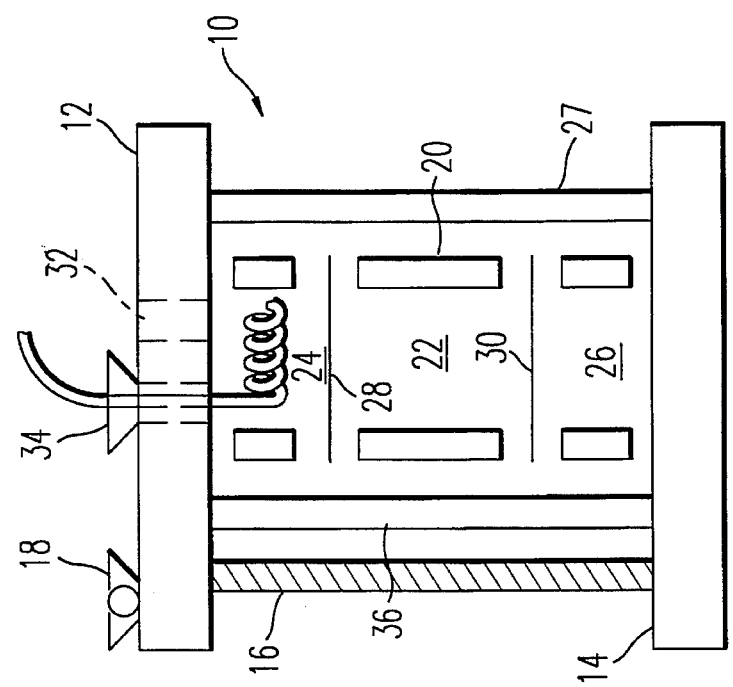
FIG. 1 is a schematic view of a perfusion chamber.

Methods and bioreactors are provided for the growth of human stem cells and/or hematopoietic cells in culture, optionally employing fibroblast cells, normally transformed, for providing growth factors, with proteinaceous components added to the mixtures of the optional fibroblast cells and human stem cells or hematopoietic cells, and either periodic intermittent or substantially continuous perfusion, optionally with recycling, to maintain an effective growth environment.

In particular, the present invention provides methods and bioreactors which provide for the maintenance of a balanced (in terms of cell types) complex primary cell culture, heretofore unobtainable. In preferred embodiments, the present invention permits co-culturing adhering human stromal cells, adhering human stem/progenitor cells, and non-adherent human hematopoietic cells.

The description of the invention may be divided into descriptions of the reactor and its internal structure, perfusion conditions, and the transformed stromal cells, e.g., fibroblasts.

Generating functioning (i) ex vivo human stem cell division or (ii) human hematopoiesis in vitro requires the following:

1. A culture chamber where the cells are grown in a pH-equilibrated liquid medium of a specified composition. The cells are placed in a (hematopoietic) bioreactor culture chamber that allows for the continuous, periodic or intermittent delivery of respiratory gases and liquid culture medium to the cells. Similarly, it allows for the continuous, periodic or intermittent removal of toxic and inhibitory metabolic products and physiologically active inhibitory compounds from the cells by medium flow or dialysis across a membrane.

2. A surface area for cell attachment and growth. An active (hematopoietic) cell culture has both adherent and nonadherent cell populations. In a hematopoietic cell culture containing human hematopoietic stem cells, the adherent cell population includes stromal cells (such as fibroblasts, endothelial cells, adipocytes, etc.) and hematopoietic cells. The nonadherent cell population is mainly comprised of hematopoietic cells, particularly more differentiated cells. The culture chamber must therefore provide a suitable surface for the attachment and growth of the adherent cell population. This surface provision needs to be in balance with the rates of gas and medium exchange.

Cell densities in the bioreactors of the present invention reach up to about seven million cells per square centimeter. It is known that the oxygen requirement for one million active cells is about 0.05 to 0.5 micromoles per hour (Thomas "Mammalian Cell Technology", ch. 5, W. G. Thilly Editor, Butterworths (1986)). Accordingly, for every square centimeter of cell growth area the bioreactor of the present invention should provide sufficient gas exchange membrane area to obtain a transfer of from 0.35 to about 3.5 micromoles of oxygen per hour. As is known, if a gas permeable membrane is used in the present reactor, such a rate of oxygen transfer depends primarily on the permeability of the gas membrane used, and, as such, the rate of oxygen being transferred through the gas membrane need not necessarily be 0.35 to 3.5 micromoles of oxygen per square centimeter of gas permeable membrane area. Similarly, the nutritional requirements of the cell culture area used in accordance with the present invention are adjusted through control of the medium perfusion rate.

The surface for cell attachment may be, but does not have to be, the same as the surface at which gases are exchanged (see item 6 below). If the medium can be supplemented with all stromally-derived components the provision of the cell growth surface may be alleviated.

3. Medium composition and perfusion: The liquid medium, having a suitable composition, in the bioreactor needs to be continuously, periodically or intermittently exchanged (vide infra). This requirement therefore demands the presence of inlet and outlet ports through which the medium exchange can be accomplished. The medium contains nutrients, growth factors, and other chemical compounds that are needed for cell growth and maintenance (vide infra). Frequently, this requirement is not completely defined and complex chemical compositions such as animal or human sera are used (vide infra).

4. Harvesting of nonadherent cells: The primary product from the (hematopoietic) bioreactor system are the (hematopoietic) cells themselves, most importantly the stem and progenitor cells. Thus, means for harvesting these cells in a clinically useful condition must be provided. Such cell harvesting may be continuous, periodic or intermittent, and if carried out during cultivation must not perturb the adherent cell layer in the bioreactor significantly. Specific mechanisms for harvesting may include the use of gravity for cell settling, and even selective harvesting by using inclined sedimentation to harvest a cell population that is enriched in stem and progenitor cells. Such harvesting can take place through a cell collection port that may or may not be the same as the port through which the medium is removed.

5. Harvesting of adherent cells: At some point in time following the establishment of an active (hematopoietic) culture it may be desired to harvest some or all of the adherent cell population. (Establishment of an active hematopoietic culture may be determined by observing cells produced by the culture or by counting non-adherent cells that can be collected from the bioreactor. In a preferred embodiment of the present invention, a stromal layer is used. Establishment of such stromal layer takes about one week (two to three weeks for confluency). Thus, the chamber and the cell growth surface need to allow for the harvest of the adherent cell population in a clinically useful condition. Mechanisms for cell harvest include, physical agitation (e.g., by shaking or rapid perfusion), biological manipulation (i.e., by applying lytic enzymes, monoclonal antibodies, or adherence blockers).

6. Delivery of oxygen and removal of carbon dioxide: The requirement of adequate levels of respiratory gases must be met. Oxygen should be supplied at adequate fluxes and at non-inhibitory levels. Physiological concentrations of oxygen correspond to about 30 to 60 mmHg. Normally, levels above about 88 mmHg inhibit cellular activity, and concentrations above about 160 mmHg may be toxic. Oxygen inhibition and toxicity is cell line dependent. Bone marrow cells are believed by the inventors to be relatively sensitive. (760 mmHg of oxygen corresponds to about 1 mM at 37° C.) The carbon dioxide produced must be removed. The bioreactor may have a free gas-liquid interface for gas exchange, but preferably a gas permeable membrane is used.

To achieve high cell densities the volumetric gas delivery rate requires the presence of a gas exchange membrane with a sufficiently high specific area (membrane area per unit volume of cell culture). Desirable cell densities are minimally about 5 to 10 million cells per ml. Therefore, for example, with one million cells per $cm^2$, about 5 to 10 $cm^2$ are needed per ml. The corresponding needed gas exchange area depends on the properties of the membrane as described supra. This membrane divides the bioreactor into two compartments; a gas chamber through which the gases flow and a cell culture chamber through which the liquid is perfused and the cells grow. The latter compartment provides both surfaces for gas exchange and cell growth and attachment. These surfaces may or may not be the same.

The area of each surface type must be balanced in terms of gas permeability and cellular respiration rates. The respiration rates are most significantly influenced by the cell density. For instance, if one million cells require 0.05 micromoles of oxygen per hour, then a culture at one million cells per ml will require the delivery of 0.05 micromoles of oxygen per hour, whereas a 10-fold denser culture of 10 million cells per ml will require 0.5 micromoles of oxygen per hour. Thus, respiration rates are directly dependent upon cell density and therefore the oxygenation and specific area of the oxygenation membrane.

Alternatively, the respiratory gases may be charged into the liquid culture medium prior to its entry into the culture chamber of the bioreactor. This charging is achieved using known methods and means for adding an oxygen-containing gas or pure oxygen to an aqueous solution. Preferably carbon dioxide is removed from the liquid culture medium. Due to the low solubility of oxygen into water such configuration calls for high liquid medium perfusion rates (e.g., for a reactor with 100 million cells per ml will consume (for slow consumer cells) 0.5 micromoles of oxygen per hour per ml of reactor. At the non-inhibitory level of 60 mmHg equal to 0.08 mM equal 80 micromoles, and would take about 10 minutes to deplete the oxygen. Thus, the liquid perfusion rate required to deliver the oxygen would be 1 ml medium per 1 ml reactor volume per 10 minutes), but eliminates the requirement of a gas exchange membrane, at the expense of high internal fluid mechanically induced shear stresses (see item 8). Such bioreactor configuration corresponds, e.g., to the bioreactor design illustrated in FIGS. 6a–e, but comprised only of bioreactor top 600 with its three ports, 609, 610 and 611, one gasket 602, and bioreactor bottom 601 from which ports 607 and 608 have been omitted.

7. High cell densities and cell loading: Hematopoiesis takes place in dense niches in vivo. Prolific hematopoietic bioreactors must therefore provide for cell growth and maintenance at high cell densities. Such cell densities should exceed a few million cells per milliliter, and preferably be in the range of 10 to 500 million cells per milliliter. Such high densities require high specific areas (e.g., the specific are requirement for 10 million cells per ml at 1 million cells per square cm is 10 $cm^2$ per ml, and similarly at 500 million cells per ml is 500 $cm^2$ per ml) for gas exchange and cell attachment. Further, cell loadings need to be sufficiently high (the lower practical limit of cell loading is about 5 to 10 million total mononuclear cells. This is because stem cells are believed to be about or less than one in a million, so that a few million cells are needed to ensure that at least one stem cell is in the sample. To obtain a clinically meaningful number of cell loadings will require about 50 to 100 million cells at least) to effectively reconstitute in vivo cell synergy. In particular, sufficient numbers (i.e., as noted above, stem cells are believed to be present in an amount of about or less than one in a million. Therefore probably at least 10 to 100 million cells are needed for an active long term culture) of early hematopoietic cells need to be present.

8. Low shear stresses: Hematopoietic and stem cells in vivo experience low fluid mechanically induced shear stresses. The (hematopoietic) cells have to be protected from detrimental shear stresses in the bioreactors. In certain cases, one needs to provide for defined levels of shear stress to reproduce certain behavior. For instance, the depletion of malignant cells may require the implementation of low shear stresses that are sufficient to lead to the physical removal of malignant cells (vide infra).

Low shear stresses can be accomplished by using low flow rates or by physical separation of the cells from rapidly perfusing medium. The low flow rates can be accomplished for instance by using an internal gas exchange membrane (illustrated in FIG. 6i) (see item 6 supra). If high perfusion rates are needed, the culture chamber of the bioreactor is separated into flowing and non-flowing (illustrated in FIG. 6h). The cells are placed in the non-flowing compartment which is separated from the flow compartment with a porous membrane that allows for the rapid exchange of media components, such as key nutrients (vide infra). If desired, the molecular cut-off characteristics of this membrane can be used to confine larger molecules that the cells produce to the non-flowing compartment.

Once these requirements are met in a functioning bioreactor module, it becomes a component of an overall system (illustrated in FIG. 9) that advantageously includes means for suitable storage of unspent medium, means for harvesting cells from the bioreactor, means for delivering gases to and removing gases from the bioreactor, means for storing spent medium and means for monitoring important variables, such as pH and dissolved oxygen tension, during cultivation.

Much effort was focused on bioreactor development for mammalian cell culture during the past decade and one might think that this technology might be directly applicable for the purposes described above. For instance monoclonal antibody production by hybridoma cells and production of therapeutic proteins such as tissue plasminogen activator (tPA), and erythropoietin (Epo) by genetically engineered cell lines resulted in a great demand for optimized mammalian cell culture systems.

Although this effort resulted in the development of efficient bioreactor systems for the production of therapeutic protein from mammalian cells, the requirements placed on a human stem cell or a hematopoietic bioreactor system are significantly different. Earlier large-scale bioreactor systems supported the growth of pure transformed mammalian cell populations that are relatively easy to grow. A hematopoietic or human stem cell bioreactor system, on the other hand, must support the growth of a mixed primary cell population, that consists of stromal cells (such as fibroblasts, endothelial cells) and hematopoietic cells at different stages of differentiation (stem cells, progenitor cells, erythroid, granulocytic and monocytic precursors). Primary human cells are much more difficult to grow in culture than transformed continuous cell lines. Most importantly, the product from a hematopoietic bioreactor system are the cells themselves, rather than a secreted protein molecule, requiring means for cell collection during cultivation. Yet additional requirements result from the intended use of the cells produced in human patients. These differences are significant and call for the development of a new generation of bioreactor systems.

The requirement of stroma and physical proximity of stroma and hematopoietic cells eliminates the possibility to use suspension cultures and microcarrier based cultivation methods. The requirement for easy cell removal makes hollow fiber modules inappropriate for cell production and furthermore it has been found by our laboratory and by others (Saronini et al (1991), paper 259e at the Annual Meeting of the American Institute of Chemical Engineers, Nov. 17–22, Los Angeles, Calif.) that hollow fiber reactors under conventional operating conditions do not support the growth of human bone marrow. The use of macroporous beads calls for enzymatic treatment of cells and complex cell harvesting procedures. Thus, the use of macroporous beads may prevent clinical utility. Further, the inventors have found that it is not possible to maintain the required cell population balance of human hematopoietic cells versus stromal cells when bone marrow is grown on macroporous collagen beads. The stromal cells overgrow the macroporous beads and suffocate all hematopoietic activity. Thus, clearly a significant need exist to provide devices and methods for cultivation of a clinically meaningful number of human stem or hematopoietic cells.

The reactor thus comprises a vessel which may be of any convenient shape which allows for the necessary cell distribution, introduction of nutrients and oxygen, removal of waste metabolic products, optional removing or recycling of hematopoietic cells, substitution of stromal cells, and harvesting of hematopoietic cells.

The reactor should provide for conditions which substantially mimic bone perfusion. In vivo, about 0.08 ml to 0.1 ml of serum per ml of bone marrow per minute is perfused. This translates into about 0.2 ml to 0.3 ml of serum per $10^6$ cells per day. Depending on cell density, the media will therefore be changed on the average between 50% and 100%, in any 24 hour period, so as to maintain a level of metabolic products which is not growth limiting. The rate of change will generally be from about 0.2 ml, preferably about 0.5 ml, to 1.0 ml of perfusion medium per $10^6$ cells per day, empirically mimicking in vivo perfusion rates. The exact rate can depend on the type of serum used.

The rate of perfusion in the bioreactor will vary depending on the cell density in the reactor. For cells cultured at $2-10\times10^6$ cells/ml, this rate is 0.25 ml/ml to 3.0 ml/ml reactor volume per 24 hours, where the medium used contains 20% serum, either 10% fetal calf serum and 10% horse serum, or 20% fetal calf serum. For higher cell densities, the perfusion rate will be increased proportionately to achieve a constant serum flux per cell per time. Thus if the cells are cultured at $5\times10^8$ cell/ml the perfusion rate will be 0.1 ml/ml reactor volume per minute.

These flow rates, matching serum and medium flux rates to cell density, are essential to stimulating the endogenous production of hematopoietic growth factors from the optional normal human bone marrow stromal cells in the culture. The hematopoietic growth factors induced by these serum and medium flux rates include GM-CSF, and may also include Kit Ligand, SCF (stem cell factor), IL-6 and G-CSF as well as other hematopoietic growth factors. These rates will be established in the bioreactors such that the shear stress from longitudinal flow experienced by the stem cells and progenitor cells at their stromal cell attachment sites are below approximately 1.0 and 5.0 dynes/square cm.

Various media may be employed for the growth of hematopoietic and stromal cells. Illustrative media include MEM, IMDM, and RPMI, which may be supplemented by combinations of 5–20% (v/v) fetal calf serum, 5–20% (v/v) calf serum, 5–50% (v/v) human serum, 5–50% (v/v) human plasma, and 0–15% (v/v) horse serum, and/or serum free media supplemented with PDGF, EGF, FGF, HGF or other growth factors to stimulate stromal cells or stem cells. To supplement the growth factors provided by the transformed fibroblasts, additional growth factors may be included in the perfusion medium, particularly where dedicated cells of a particular lineage are desired. Among the growth factors which may be included in the perfusion medium, either by stromal cell secretion or addition, are GM-CSF, G-CSF, or M-CSF, interleukin 1–7, particularly 1, 3, 6, and 7, TGF-$\alpha$ or $\beta$, erythropoietin, or the like, particularly human factors. Of particular interest is the presence of about 0.5–20, preferably 5–10, ng/ml GM-CSF, and 0.5–2, preferably 1, ng/ml of 1L-3, as well as a 0.1–2 U/ml of final concentration of erythropoietin, from about 100–300 ng/ml of G-CSF and about 1–100, preferably about 10, ng/ml of stem cell factor (SCF, MGF, also referred to as Mast Cell Factor or Kit ligand). In an embodiment of the invention one or more, preferably at least two, of the growth factors are provided by secretion from transformed cells, which are present in an amount sufficient to maintain the desired level of the growth factors in the perfusion medium.

Conveniently, in the reactor, physiologic temperature will be employed, namely 37° C., although lower temperatures may also be employed, including 33° C., but usually not below 25° C. Humidity will generally be about 100%, where the oxygen-containing gas, e.g., air or a gas containing 1–50% (v/v), preferably 5–20% (v/v), $O_2$, will contain about 5% (v/v) carbon dioxide. The perfusion medium may be oxygenated external to the reactor or internal to the reactor, various means being provided for internal oxygenation. Internal oxygenation may be achieved with porous sintered disks, silicone tubing or other membranes of suitable porosity and hydrophobicity. The nutrient level and metabolic product level will normally be maintained in a relatively narrow range. Glucose level will usually be in the range of about 5 to 20 mM, usually about 10 below about 35 mM and may be allowed to be over 20 mM. Glutamine concentration will generally be maintained in the range of about 1 to 3 mM, usually 1.5 to 2.5 mM, while ammonia concentration will usually be maintained below about 2.5 mM, preferably below about 2.0 mM.

The flow of fluid may be by gravity, by a pump, or other means, where the flow may be in any direction or a multiplicity of directions, depending upon the nature of the internal structure of the reactor. Desirably, laminar flow may be employed where the flow may be substantially horizontal across the reactor or vertical flow may be employed, where the flow is from the bottom to the top of the reactor or vice-versa.

Where the source of human hematopoietic cells is suspected of having neoplastic cells, e.g., leukemic lymphoma or carcinoma, the perfusion flow can be selected so an to segregate the normal progenitor cells from the neoplastic hematopoietic cells. It is found that normal hematopoietic progenitor cells adhere to stroma and matrix proteins with an affinity able to withstand approximately 1.5–2.0 dynes/cm$^2$ stress from longitudinal fluid flow. By contrast, neoplastic cells and their progenitors have a substantially weaker affinity for stroma, in the range of about 0.05–1.2 dynes/cm$^2$. By providing for a perfusion flow rate which provides shear stress rates intermediate between that tolerated by normal and neoplastic progenitor cells, generally greater than 1 dyne/cm$^2$, one can provide for separation of the neoplastic progenitor cells from the normal progenitor cells, generally maintaining the perfusion for at least about two days, preferably at least about five days, and more preferably seven days or more.

In this manner, one can expand normal hematopoietic cells from a human patient, while at the same time using the appropriate flow rates, separate neoplastic cells. In this manner, one can provide for autologous hematopoietic cells from a patient suffering from neoplasia, expand the normal hematopoietic cells during a period of treatment of the patient by chemotherapy or X-ray irradiation, and then restore normal hematopoietic cells to the patient to restore hematopoiesis and the immune system of the patient.

Illustrative of the use of shear stress to separate hematopoietic tumor cells from normal hematopoietic cells is the situation of chronic myelogenous leukemia (CML). Shear stress tolerance for CML cells is in the range of 0.05–1.2 dyne/cm$^2$. This difference permits the efficient removal of CML cells with an individual bone marrow sample. By employing a shear stress of about 1.2–1.5, preferably 1.3, dynes/cm$^2$ the CML cell may be efficiently separated.

The shear stress tolerance within an individual's bone marrow cells may be determined using a tapered radial flow chamber. In the radial flow chamber, the shear stress experienced by the cell decreases with distance "d", from the start of the chamber an a function of 1/d. Bands of cells may then be analyzed for cell population and the shear stress set for the desired cell population to be retained. For the removal of leukemic stem cells, progenitor cells and stem cells from bone marrow samples from patients with leukemia are first placed into a radial flow chamber.

The radial flow chamber consists of two parallel plates, made of polycarbonate or glass, which permit the adhesion of bone marrow stromal cells to the lower plates. The initial measurements can be performed by either (1) establishing a preformed confluent monolayer of bone marrow stromal cells prior to hematopoietic cell infusion and then initiating fluid flow after 12–24 hours, or (2) inoculating the patient's bone marrow directly into the flow chamber without using a preformed stromal monolayer, and then waiting 3–4 days before establishing the fluid flow, usually 0.05–1.0 cc/min. The exact flow rate to achieve a desired shear stress will depend on the separation of the parallel plates.

The plates are sealed together at the edges through a rubber gasket, and held together with adjustable screws. At the narrow, infusion, end of the chamber a tube brings fluid into the chamber from a reservoir delivered by a constant pressure (e.g., syringe-type) pump. At the wide, collection end, the fluid and removed cells are collected through a separate tube (see FIGS. 3a and 3b). After the period of perfusion (usually 3–7 days), the nonadherent cells are removed, and the plates are separated, cells from each of 3–5 regions are separately removed by aspiration and rubber policeman, and each fraction is analyzed for the presence of leukemic cells by standard techniques (usually karyotypic analysis by chromosomal banding). Comparison of the leukemic analyses of each fraction demonstrates in which fraction (i.e. at which shear stress), the leukemic cells fail to adhere to the stroma and are removed. In these chambers, the shear stress perceived by the cells declines exponentially as a function of the distance are from the inlet. (See FIG. 3c.) Typically, the nonadherent cells are all or nearly all leukemic, whereas cells adhering at the in the narrowest ½ of the chamber are all or nearly all normal.

Based upon the results of these measurements, a series of parallel, rectangular chambers is established in which the rate of fluid flow (see FIGS. 4a and 4b) over the lower surface creates a shear stress rate which was found in the tapered chamber to remove leukemic cells from the stroma without removing all of the normal cells. In the case of chronic myelogenous leukemia patient bone marrows, this shear stress is typically 0.01–0.5 dynes/square cm. The actual flow rate employed will depend on the size and geometry of the chambers. Bone marrow cells from the patient will be cultured in these rectangular chambers at a concentration of 5×10$^6$/ml to 50×10$^6$/ml in Iscove's Modified Dulbecco's Medium with 5–20% (typically 10%) fetal calf serum plus 0–14% (typically 10%) horse serum, with or without 10$^{-6}$M hydrocortisone. The bone marrow cells will be cultured for 12–24 hours without fluid flow, and then fluid flow will be initiated. The cells will be cultured for 3–7 days, at which time all of the nonadherent cells will be discarded. The adherent cells will be recovered from the rectangular plates by aspiration and mechanical agitation, and then collected. These cells can then be either directly returned to the patient, or stored in liquid nitrogen by standard techniques for later use.

Cells other than those of the hematopoietic system also may be separated using differential tolerance to shear stress. Thus, where there are distinct subpopulations of cells within a complex mixture of cells the methods described above can be used to separate out a cell type of interest from within a suspension of cells derived from, e.g. skin, liver, muscle, nerve, or epithelium. Of particular interest is the separation of tumor cells from within a population of normal cells. The population of cells to be separated will be contacted with a suitable stromal substrate as described below, such as a purified protein or cellular component to which the cells of interest adhere. The shear stress tolerance for each of the adherent subpopulations is determined an described above. The fluid flow can then be adjusted appropriately so as to retain the desired subpopulation of cells on the stroma. The desired cells are then collected as described above.

A variety of packings may be used in the reactor to provide for adherent growth of the cells, while maintaining some physical separation between the stromal cells and the hematopoietic cells, and while allowing for some contact or close juxtaposition between the stromal cells and the hematopoietic cells. In this way, the factors secreted by the stromal cells may be readily taken up by the hematopoietic cells to encourage their proliferation and, as appropriate, differentiation and maturation.

The protein matrix to support the cells may take the form of shredded collagen particles, e.g., sponges or porous collagen beads, sponges or beads composed of extra-cellular bone matrix protein from bone marrow, or protein coated membranes, where the protein may be collagen, fibronectin, hemonectin, RGD-based peptide, mixed bone marrow matrix protein, or the like. Pore sizes of membranes will generally range from about 1 to 5µ to allow for interaction between the different cell types, while still retaining physical separation.

Membranes may be employed, which will be protein coated. Various membrane materials may be employed such as polypropylene, polyethylene, polycarbonate, polysulfonate, etc. Various proteins may be employed, particularly collagen or the other proteins which were indicated previously. The membrane should have sufficiently small pores, that the transformed cells may not pass through the membranes, but may grow and form a confluent layer on one side of the membrane and extend portions of the cell membrane into the pores. Generally the pores will be in the range of about 1 to 5µ. In this manner, the hematopoietic stem cells may grow on the opposite side of the membrane and interact with the transformed cells, whereby factors may be transferred directly from the transformed cells to the hematopoietic progenitor cells. The progenitor cells and the stem cells, are able to attach to the intruded cytoplasmic projections which have passed into the pores. Hematopoietic differentiation from the stem cells occurs on one side of the membrane and differentiated progeny are unable to squeeze back through the pores, which are already largely occupied by the stromal cell layer when confluence is approached or reached, (i.e., cytoplasmic projections from the fibroblasts). As hematopoietic cells mature and differentiate, they will be released from the membrane and into the nutrient medium.

The reactor may be packed with the various particles in a central portion of the reactor to define a central chamber, which will be separated from an upper chamber and a lower chamber. Alternatively, one or a plurality of membranes may be introduced, where two membranes will define a region associated with either the stromal cells or the hematopoietic cells, where the regions will alternate between stromal and hematopoietic cells. In this way, one may provide for differential perfusion rates between the chambers of the hematopoietic cells and the stromal cells. The medium exchange rate will generally fall within the ranges indicated above.

For example, one could provide for a plurality of chambers in which stromal cells may grow and the hematopoietic cells may be moved in accordance with the chamber which has the stromal cells at a subconfluent level. Thus, by having a movable barrier between the chambers, when the stromal cells approach confluence, generally after about 8–12 days, one could open or remove the barrier between the chambers and allow for the stromal cells to migrate into the new chamber and allow for the hematopoietic cells to come in contact with the subconfluent stromal cells, while the subconfluent stromal cells feed the factors to the chamber comprising the hematopoietic cells (see FIG. 5a and FIG. 5b).

The transfer of the hematopoietic cells can be achieved by appropriate flow rates or by other convenient means. One can provide for various wells in the chamber, which are divided by appropriate walls, after seeding in one well, when the cells become confluent, cells will then move over into the next well and seed the next well in a subconfluent manner. Another modification of the system is one in which, after 8–12 days in culture, the hematopoietic cells are exposed to now, proliferating stromal cells. This is accomplished in one of several ways. This exposure to proliferation stromal cells is accomplished in one of several ways.

In the first technique, the culture are several ways, exposed to EDTA for 3–5 minutes, which removes the hematopoietic stem cells from the stromal cells. The removed cells are then transferred to a new culture vessel, which may itself contain bone marrow stromal cells seeded 3–7 days prior. This process in repeated every 8–12 days. Another alternative approach is to add additional surface area by increasing the volume of the cultures and adding additional collagen beads to the cultures at 8–12 days. Finally, small organic molecules or proteins, particularly hormones, such as platelet-derived growth factor (at 100–500 ng/ml), interleukin 1 alpha, tumor necrosis factor alpha, or basic fibroblast growth factor or other molecules mitogenic to fibroblasts, can be added to the cultures every 3–7 days. This exposure to stromal mitogenic stimulatory factors promotes the continued proliferation of bone marrow stromal cells, and their continued production of hematopoietic growth factors. Thus, one can provide for the continuous subconfluent stage of the stromal cells.

Continuous fluid flow can also be used to selectively separate normal from cancerous cells within a bone marrow population. In this approach, a radial flow chamber is first used to determine the specific stromal adhesive properties of normal versus cancerous cells, and then a rectangular flow chamber with flow rates established to achieve a shear stress sufficient to remove the cancerous cells is used to preoperatively separate the normal and cancerous cells.

The subject method and apparatus also provides for the opportunity to recycle stem cells which are lost by the flow of the perfusion medium. The surface membrane protein marker CD34 substantially separates mature hematopoietic cells from mature hematopoietic cells. Thus, by capturing and recycling those cells which are $CD34^+$, one may avoid the lose of stem cells to the medium.

Various techniques may be employed for capturing and returning the immature fraction of cells to the reactor. For example, one could label the cells with an antibody specific for CD34 and then use antibodies to the antibody for collecting the $CD34^+$ cells and recycling them to the reactor. Alternatively to positive selection, one may use negative selection, whereby one would remove the mature cells employing antibodies to various markers associated with mature cells, such as antibodies to glycophorin A, CD33, M01, OKT3, OKT4, OKT8, OKT11, OKT16, OKM1, OKM5, Leu7, Leu9, Leu M1, Leu M3, and the like. Various antibodies are available for markers specific for mature cells of the various hematopoietic lineages, lymphoid, myeloid and erythroid, and these antibodies may be used to remove the mature cells from the effluent from the reactor, followed by harvesting of the remaining cells and restoring them to the reactor. In this way, one can avoid forced decline in the cultures due to loss of stem cells and maintain unlimited stem survival in vitro.

Separation using antibody markers can be achieved in various ways, using standard techniques, individually or in combination, such as panning, fluorescence activated cell sorting, antibodies bound to various surfaces, e.g. polystyrene surface, metal microspheres and magnets, and the like. The antibodies are bound to a surface which allows for separation between adherent and non-adherent cells or the antibodies are labeled, directly or indirectly, which permits selection between labeled and unlabeled cells.

By following the subject procedures greatly extended periods of in vitro growth of hematopoietic cells may be achieved, generally providing ex vivo human hematopoiesis for at least six months in culture, with granulopoiesis being supported for at least four months and erythropoiesis for at least three months. In addition, hematopoietic progenitor cells are continuously generated throughout the culture resulting in net expansions of progenitor cells of over 10-fold from input cells.

In addition, by following the subject procedures greatly increased rates of stem cell division are supported, permitting the efficient insertion of retrovirally transfected genetic material. Genes inserted by the appropriate retroviral vector during an initial two week infection period can be expressed in up to 10–30% of all progenitor and precursor cells arising during subsequent culture for over four months in culture. These subject procedures thus support the successful transfer of genetic material into a highly proliferative human hematopoietic stem cell.

In the figures like reference numerals designate identical or corresponding parts throughout the several views. FIG. 1 thereof, FIG. 1 is a schematic view of a perfusion chamber. Reactor 10 with cover plate 12 and floor plate 14 are joined by bolts 16, held in position by wing nuts 18. Three bolts are employed, so as to avoid warping.

The chamber 20 has three sections, the middle section 22 containing the support matrix for the stromal cells, the bed of stromal cells, and the bone marrow cells. The central section 22 is separated from the top section 24 and the bottom section 26 by membranes or mesh 28 and 30 respectively. Conveniently, a polysulfone membrane may be employed or a stainless steel mesh, whose mesh size is small enough so that cells are contained within the central section of the chamber. The separating interphase may be placed in the chamber using an inner cylinder 27 which is sectioned to provide the separating membrane mechanical support. The top section 24 and the bottom section 26 need not be identical and will have tubing or membranes across which liquid media and gases are exchanged. The gases are exchanged across a hydrophobic, e.g., silicone, tube whose length (and thereby gas/liquid contact area) may be varied to allow for sufficient gas fluxes to support the needs of the cell population that is metabolizing in the central section. The media can be pumped or withdrawn directly from the top or bottom sections through port 32 and may be fed through delivery tube 34.

If desired, the top and bottom sections may be eliminated by using an external oxygenator. In this situation, the separating membrane is held in place under the glass cylinder 36 which fits into cylindrical groove plates 12 and 14 and the area inside of the cylindrical groove is indented to allow for good flow distribution across the membrane. This geometry allows the fluid from the finite number of inlet ports to mix and for radial pressure to equilibrate, leading to a uniform liquid flow across the separating membrane. This setup in suitable for chambers which have relatively few cells, so that oxygenation does not become limiting.

Figure 2:
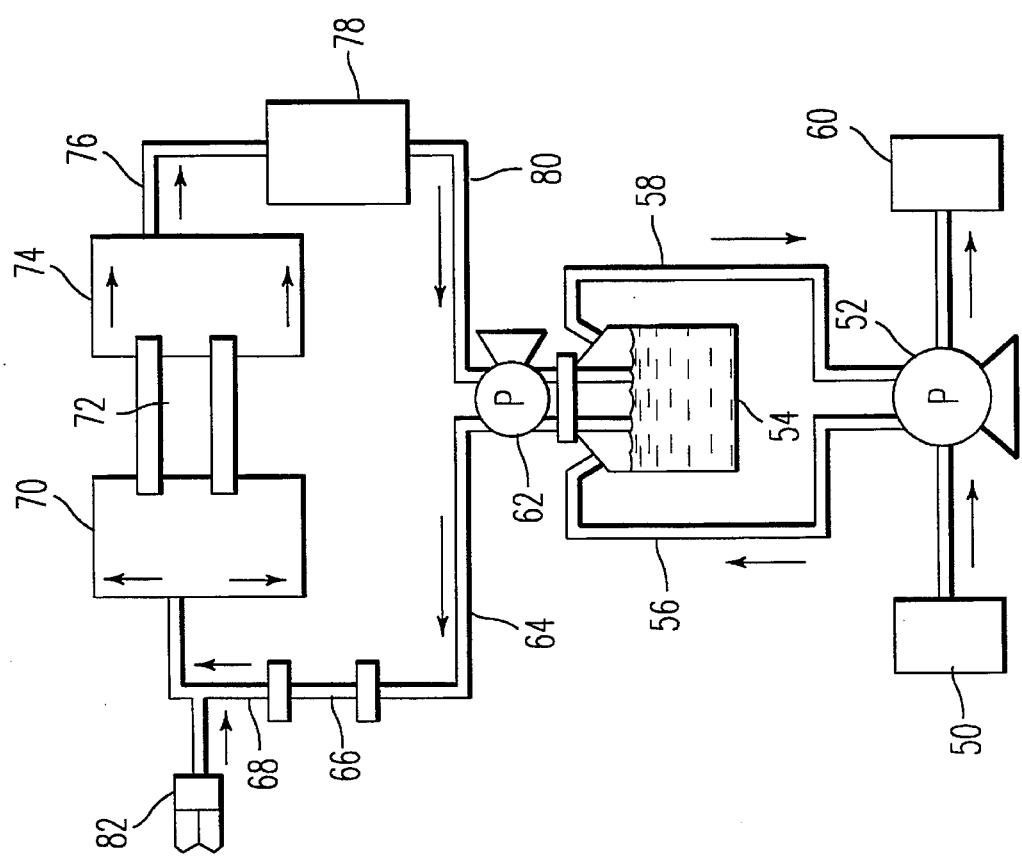
FIG. 2 in a schematic representation and flow diagram of the perfusion medium pathway.

In FIG. 2 is depicted a schematic representation of the loop that connects the perfusion chamber to the side media reservoir, oxygenator, sensor chamber, and sample/injection ports.

An external fresh media source 50 is pumped by means of pump 52 to a media reservoir through line 56 and spent media is withdrawn through line 58 from reservoir 54 by means of pump 52 to the spent media container 60 for further processing. A second pump 62 pumps media from the media reservoir 54 through line 64 through a hollow fiber oxygenator 66. The media is directed through line 68 to the first chamber of bioreactor 70. An appropriate, a means for injection of media component 82 in provided, for introducing the component into line 68 for transport by the media into the first chamber of bioreactor 70. The component may be test components, additional factors, or the like. The media from bioreactor 70 is directed through central chamber 72 into the second chamber 74 of the bioreactor. From there the media is directed by line 76 to in-line sensors 78 for detecting the change in composition of the media.

For example, it is desirable that the glutamine:glucose (wt./wt.) ratio be in the range of about 1:5–8, depending on the cell lines used; for instance, preferably 1:8 for transfected 3T3 cells. Furthermore, ammonium concentrations will preferably be below about 2.0 mM and lactate concentrations are preferably less than about 35 mM. By monitoring the effluent from the bioreactor, the media introduced into the bioreactor may be modified, oxygen partial pressure may be changed, gas flow rate may be altered, various components may be augmented, or the rate of perfusion may be slowed or increased. From the sensors 78, the media is directed through line 80 by means of pump 62 to the reservoir 54.

By means of the flow path described above, the media in the side reservoir is slowly exchanged using a separate pump. This organization allows for separate control of the media exchange rate (the outer pump) and the flow rate through the oxygenator and perfusion chamber. The former is used to control the longer term change in the media composition and perfusion, while the latter may be used to control the dissolved oxygen tension and flow patterns in the chamber. The use of a small mesh biocompatible membrane allows for plug (piston) flow in the chamber and thus allows the precise control of delivery of growth factors and other special compounds that one may wish to introduce to the hematopoietic cells and stromal cells in very precise amounts.

After autoclaving the chamber and components of the loop, the reactor is assembled in a sterile environment. The media may be circulated through the side loop and chamber for a few days while signs of contamination are monitored. If sterile assembly in accomplished, the central section of the chamber is inoculated with either the extra-cellular matrix alone or a preinoculated extra-cellular matrix support that contains the stromal cells. The stromal cells are then either: (1) kept in the chamber for a period of a few days while their metabolic performance and/or growth factor responsiveness is monitored and if results are satisfactory, the bone marrow is inoculated; or (2) immediately seeded with bone marrow.

In either case, the cell layer is kept at the bottom of the central section of the perfusion chamber. The cells lay down additional extra-cellular matrix and the cell layer adheres to the separating membrane. At this time, the chamber may be inverted and the cell layer may then be located at the ceiling of the central section. In this configuration, the maturing cells will settle on the bottom of the central chamber as they lose their adherence to the stromal layer. This feature is important to prevent the damage caused by mature cells to the stromal layer and/or the less mature hematopoietic cells. This feature also makes the continuous removal of mature cells easier.

These cells are harvested by withdrawing the cells by syringe, or by continuously allowing the cells to flow out of the chamber, by the pressure of the perfused medium, through the exit tubing.

The stromal cells will, for the most part, be fibroblasts transformed with one or more genes providing for desired hematopoietic growth factors. The same or different cells may be transfected with the genes, depending upon the particular selection of host cells, the same or different cells may be used for a plurality of genes.

A wide variety of normal cells or stable lines may be employed. However, it is found that not all cell strains are permissible, since transformation of some cell lines may result in the overgrowth of the cells. Desirably, the cells which are employed will not be neoplastic, but rather require adherence to a support. The mammalian cells need not be human, nor even primate. A variety of nontransformed cells may be included in the adherent cell layer as well, including normal human bone marrow adherent cells, normal human spleen adherent cells, and normal human thymic epithelium.

Methods for transforming mammalian cells, including fibroblasts, are well known and there is an extensive literature of which only a few references have been previously given. The constructs may employ the naturally occurring transcriptional initiation regulatory region, comprising the promoter and, as appropriate the enhancer, or a different transcriptional initiation region may be involved, which may be inducible or constitutive.

A large number of transcriptional initiation regions are available which are inducible or constitutive, may be associated with a naturally occurring enhancer, or an enhancer may be provided, may be induced only in a particular cell type, or may be functional in a plurality or all cell types. The transcriptional initiation region may be derived from a virus, a naturally occurring gene, may be synthesized, or combinations thereof.

Promoters which are available and have found use include the chromosomal promoters, such as the mouse or human metallothionein-I or II promoters, actin promoter, etc., or viral promoters, such as SV40 early gone promoters, CMV promoter, adenovirus promoters, promoters associated with LTRs of retroviruses, etc. These promoters are available and may be readily inserted into appropriate vectors which comprise polylinkers for insertion of the transcriptional initiation region as well as the gene of interest. In other instances, expression vectors are available which provide for a polylinker between a transcriptional initiation region and a transcriptional termination region, also providing for the various signals associated with the processing of the messenger for translation, i.e., the cap site and the polyadenylation signal. The construction of the expression cassette comprising the regulatory regions and the structural gene may employ one or more of restriction enzymes, adapters, polylinkers, in vitro mutagenesis, primer repair, resection, or the like.

The expression cassette will usually be part of a vector which will include a marker and one or more replication systems. The marker will allow for detection and/or selection of cells into which the expression cassette and marker have been introduced. Various markers may be employed, particularly markers which provide for resistance to a toxin, particularly an antibiotic. Preferably, neomycin resistance is employed, which provides resistance to G418 for a mammalian cell host. The replication systems may comprise a prokaryotic replication system, which will allow for-cloning during the various stages of bringing together the individual components of the expression cassette. The other replication system may be used for maintenance of an episomal element in the host cell, although for the most part the replication system will be selected so an to allow for integration of the expression cassette into a chromosome of the host.

The introduction of the expression cassette into the host may employ any of the commonly employed techniques, including transformation with calcium precipitated DNA, transfection, infection, electroporation, ballistic particles, or the like. Once the host cells have been transformed, they may be amplified in an appropriate nutrient medium having a selective agent, to select for those cells which comprise the marker. Surviving cells may then be amplified and used.

Host cells which may be employed include African green monkey cell line CV1, mouse cells NIH-3T3, normal human bone marrow fibroblasts, human spleen fibroblasts, normal mouse bone marrow fibroblasts, and normal mouse spleen fibroblasts. It should be noted that in some instances, depending upon the choice of vector and cell line, the cells may become neoplastic. It is important that the resulting transformed cells be capable of adherence, whereby the transformed cells maintain binding to a support, Such as protein sponges, protein coated membranes, or the like.

Once the vector for expressing the appropriate growth factors has been constructed, it may be used to transform the cells by any convenient means. The resulting transformed cells may then be used to seed the supports, which have already been described. These supports may be introduced into the reactor or may be present at the time of seeding in the reactor. The cells will be allowed to grow for sufficient time to ensure that the cells are viable and are capable of producing the desired growth factors.

The reactor may then be seeded as appropriate with the hematopoietic cells. The hematopoietic cells may include substantially pure stem cells, a mixture of hematopoietic cells substantially free of mature hematopoietic cells of one or more lineages, or a mixture comprising all or substantially all of the various lineages of the hematopoietic system, at various stages of their maturation.

The cells are allowed to grow with substantially continuous perfusion through the reactor and monitoring of the various nutrients and factors involved. For the most part, the primary factors will be provided by the stromal cells, so that a steady state concentration of growth factors will normally be achieved. Since conditioned supernatants are found to be effective in the growth of the hematopoietic cells, one can provide for a ratio of stromal cells to hematopoietic cells which will maintain the growth factor at a appropriate concentration level in the reactor.

Transfected stroma can provide for the introduction of genes into human stem cells. In mice, retroviral mediated gene transfer into stem cells is made possible by pretreating mice with 5-FU and then growing the harvested bone marrow cells in WEHI conditioned media, which contains IL-3 and GM-CSF (Lemischka, *Cell* (1986) 45: 917). The artificial stroma, grown with a retroviral packaging cell line secreting a retroviral vector of interest, may be used to efficiently introduce genes into human stem cells. For example, human T-cells could be made resistant to HIV infection by infecting stem cells with the retroviral vector containing an HIV antisense sequence under control of a CDC2 regulatory sequence (Greaves, *Cell* (1989) 56: 979–986) which would allow for tissue specific expression in T-cells. There would be a factor provided by the retroviral packaging cell line essential for replication of the retrovirus; this factor would be absent in the hematopoietic target cells. Once the virus was transferred to the hematopoietic target cells, it would no longer be able to replicate.

Figure 3A:
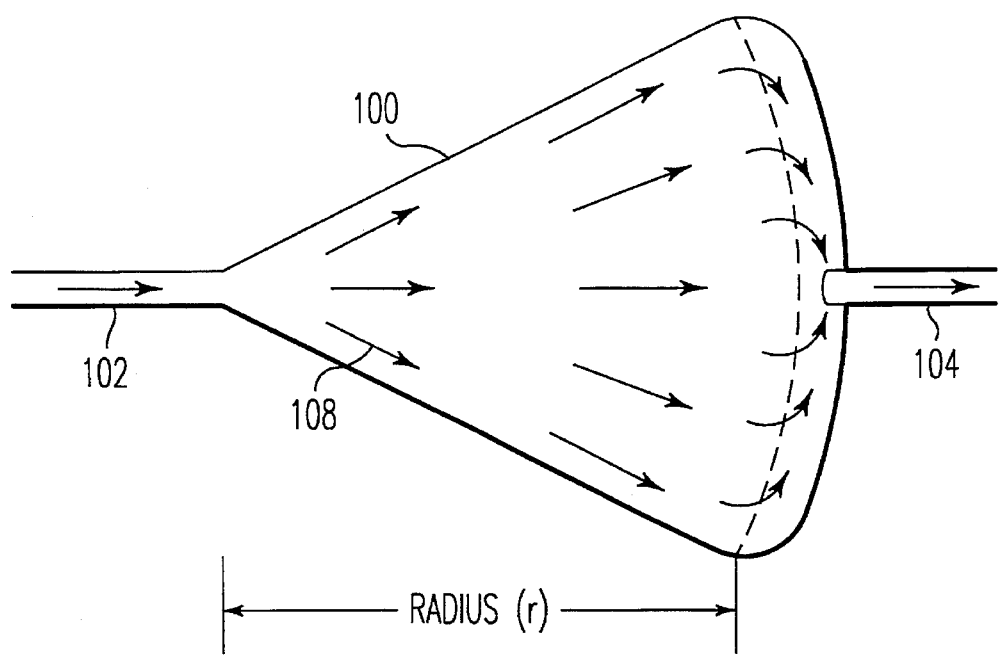
FIG. 3a is a schematic view of a flow chamber for measuring shear stress for separation of cells.
Figure 3B:
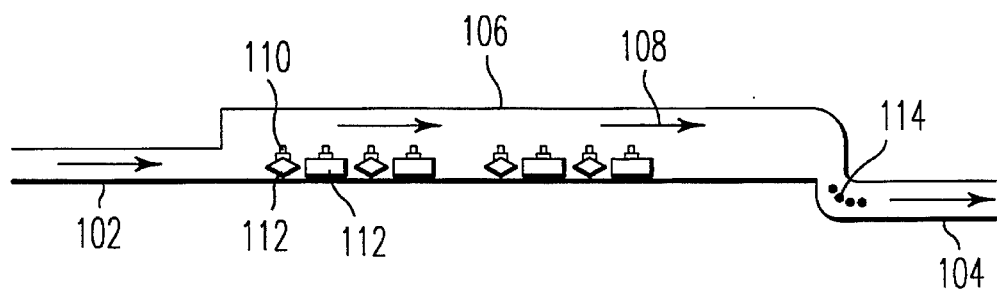
Figure 3C:
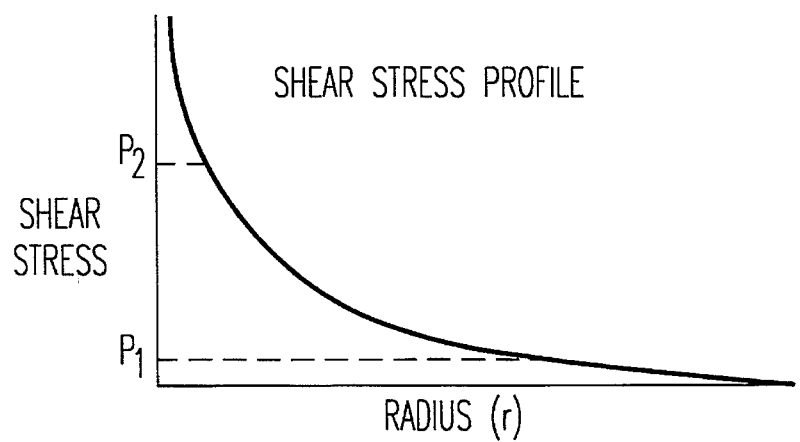
FIG. 3c is a graph of a shear stress profile for hematopoietic cells.
Figure 4A:
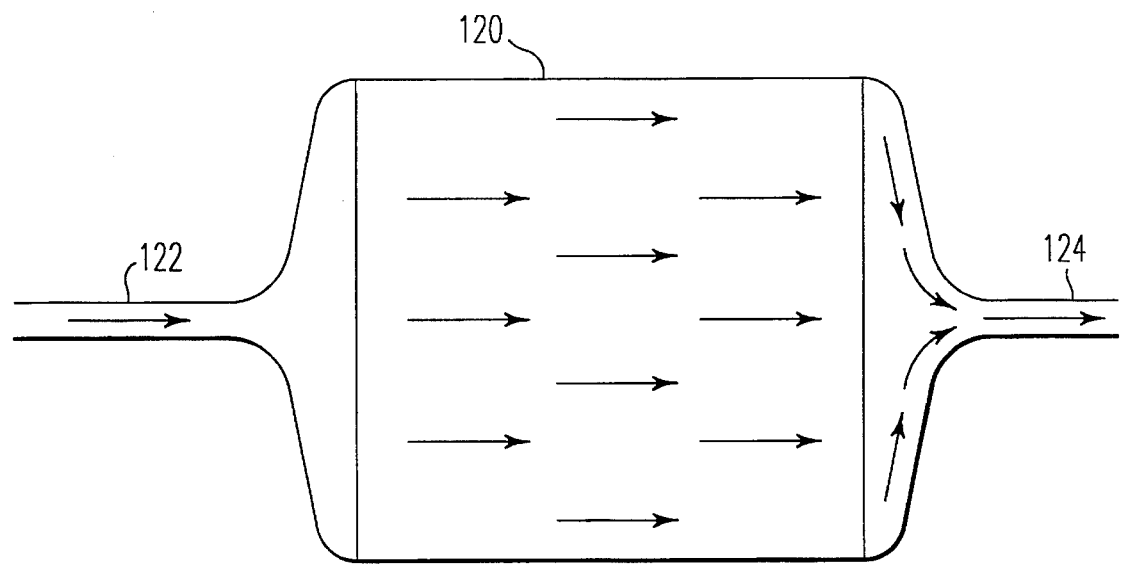
FIGS. 4a and 4b are top and side views of a flow chamber for growing and separating hematopoietic cells.
Figure 4B:
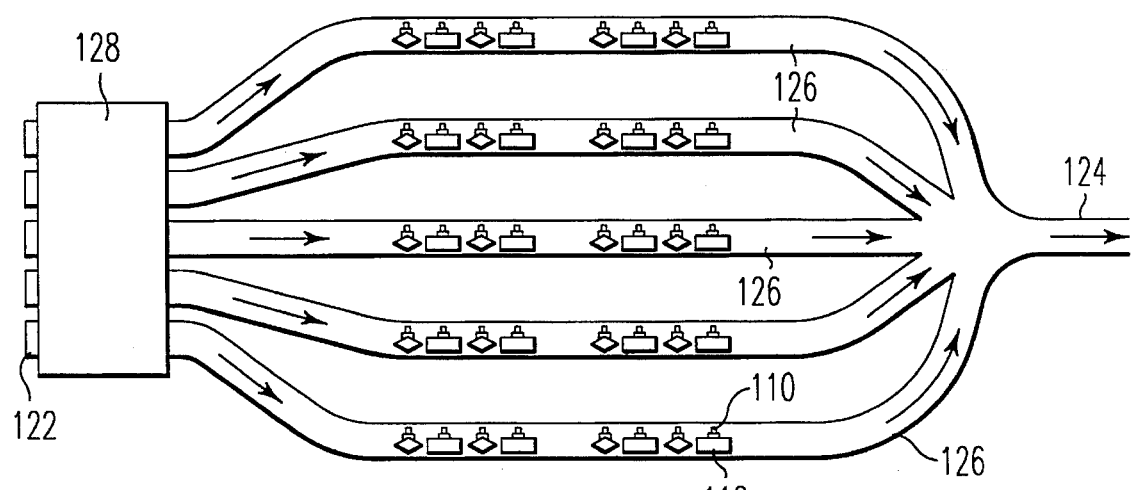

In FIGS. 3a and 3b are depicted radial flow chamber 100 having inlet 102 and outlet 104, and with chamber 106 where the arrows 108 indicate the direction of flow. Hematopoietic cells 110 are seeded onto a stromal layer 112 in the chamber and grown. The flow rate will determine which cells are able to adhere, the non-adherent cells 114 passing out through outlet 104. As is evident from FIG. 3B, the stromal layer 112 is located, for example, in the lower portion of the chamber 106 so that the flow path indicated by the arrows 108 is substantially unobstructed by the stromal layer. The cell culture medium may therefore freely flow through this fluid flow path. In FIGS. 4a and 4b, growth chamber 120 is provided having inlet 122 and outlet 124. In FIG. 4b, inlet 122 comprises a manifold 128 which feeds individual chambers 126 containing cells 110 and stroma 112 in the chamber 126 for growth and separation.

In FIGS. 5a and 5b are shown growth chambers in which barriers 134, 136, 138 are removed sequentially during culture: barriers 134 at about week 8–10; barrier 136 at about week 18–20 and barrier 138, at about week 28–32.

In a preferred embodiment, the components of the (hematopoietic) bioreactor system are grouped into two parts. First, the bioreactor unit itself that needs to meet the itemized list of requirements that is outlined above. Second, the components that are auxiliary to the bioreactor module and provide necessary systemic aspects of the whole process.

I. The bioreactor.

Figure 11A:
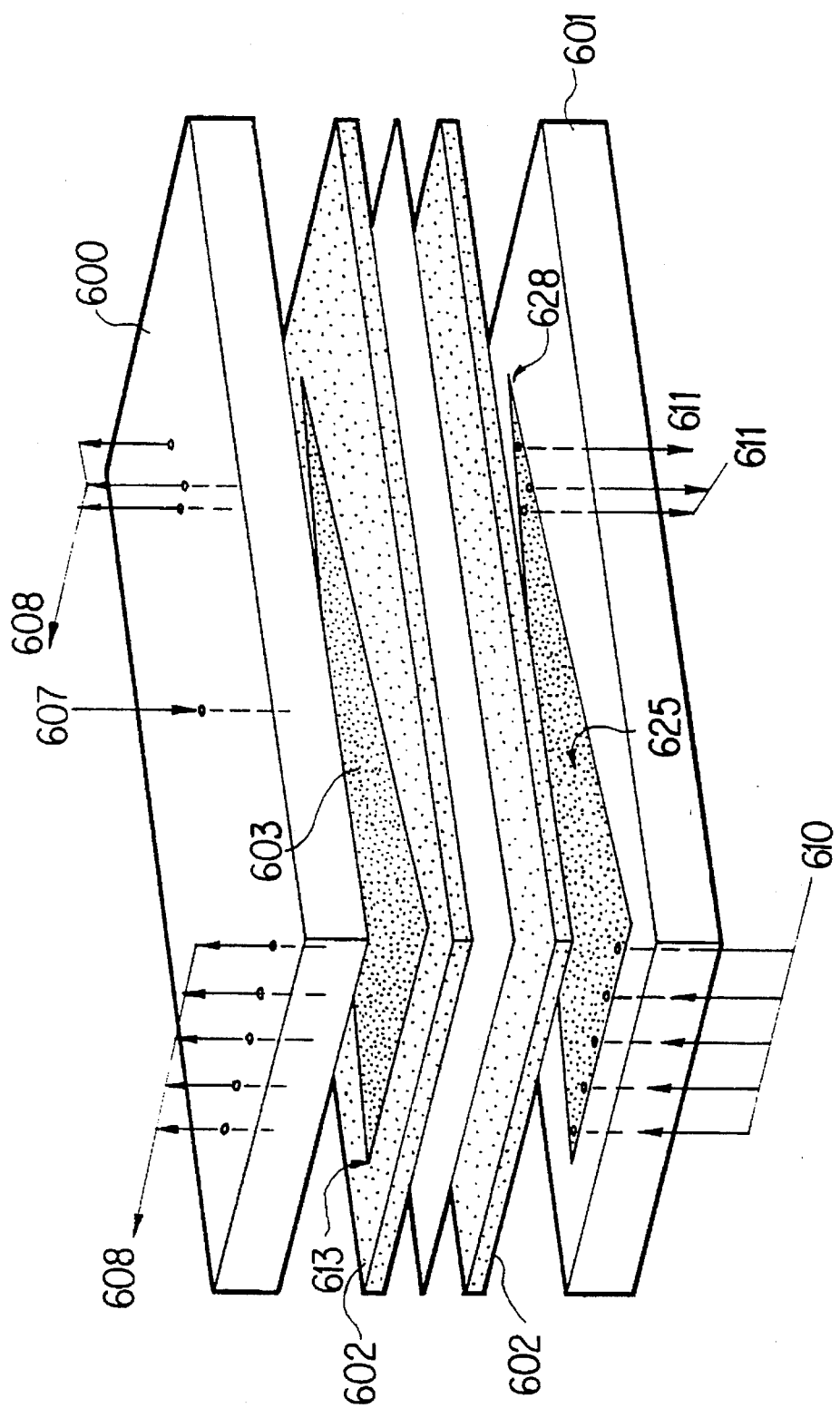
FIGS. 11a–11c illustrate a bioreactor designed in accordance with the present invention, specifically adapted for cell harvesting, including selective cell harvesting.
Figure 11B:
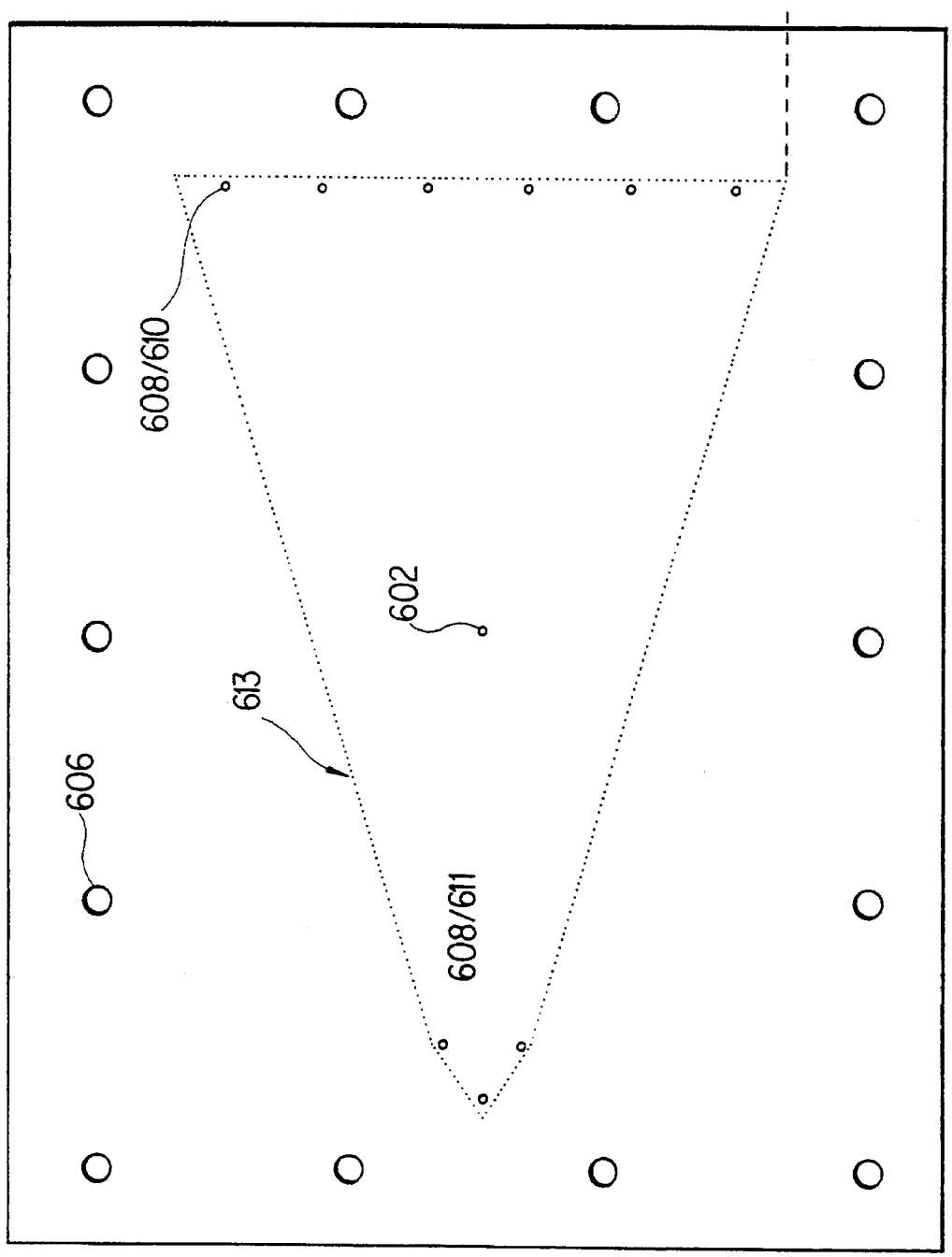
Figure 11C:
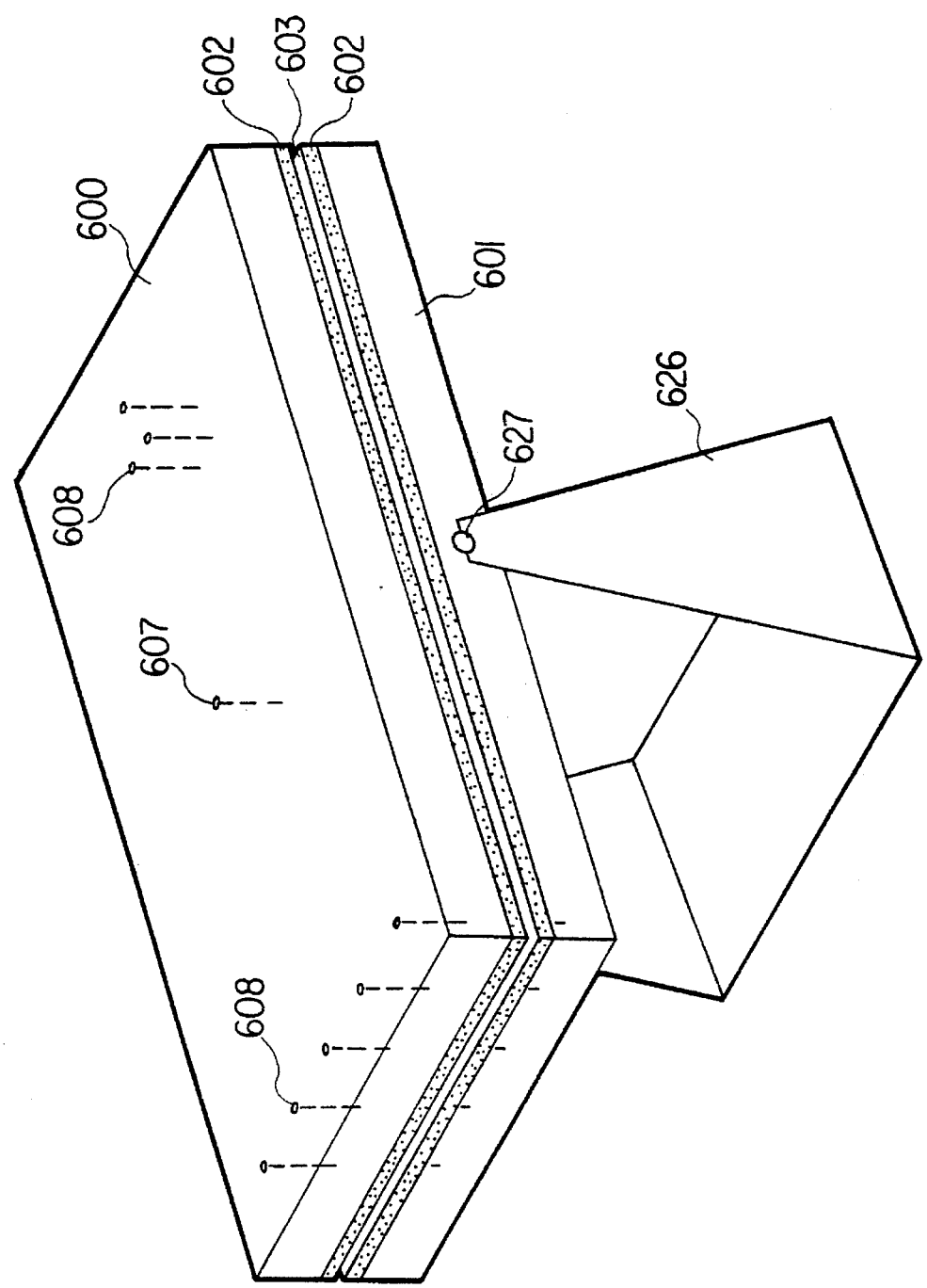

The specifications for the (hematopoietic) bioreactor enumerated above can be embodied in varied ways. Three preferred embodiments described here are: (1) a flat-bed (hematopoietic) bioreactor (FIGS. 6a–i), (2) a flat-bed (hematopoietic) bioreactor with a conical section for cell sampling harvesting (FIGS. 7a and b), (3) an inclined (hematopoietic) bioreactor (FIGS. 8a and b), and (4) an horizontal or inclined bioreactor with a tapered flow profile (FIGS. 11a–c). These four embodiments will now be described in greater detail.

I.1. Flat-bed (hematopoietic) bioreactor with single or multiple surfaces:

This bioreactor comprises at least two machined or molded flat pieces, 600 and 601, made from materials which are nontoxic to the cells being cultured, such as polycarbonate, polysufone, polystyrene, etc., forming a bioreactor top, 600, and a bioreactor bottom, 601, or vice versa, and between the bioreactor top and bottom, 600 and 601, two gaskets, 602, which may be made from any material suitable for making gaskets which is nontoxic to the cells being cultured, such as silicone rubber.

When the bioreactor is assembled, as illustrated in FIGS. 6f–i which provide various embodiments of the bioreactor, a membrane 603 is placed between the two gaskets 602 and this assembly is in turn placed between the bioreactor top 600 and the bioreactor bottom 601. The whole assembly may be held together by any known suitable means, such as clamps or bolts (the latter being illustrated in the Figures). Holes 606 through which bolts may be inserted are shown in FIGS. 6a–e, however other bolt configurations are possible. When assembled, an enclosure defining two chambers are created, one for cell culture 614, the other a gas chamber 615. Bioreactor top 600 and bioreactor bottom 601 may have different numbers of ports. For example, in FIGS. 6a–e bioreactor bottom 601 is shown having two gas ports 607 and 608, one for gas inlet and one for gas outlet, or vice versa, whereas the bioreactor top 600 is shown having three ports: a liquid medium inlet port 610 and a liquid medium outlet port 611, or vice versa, and a cell sampling or harvesting port 609 (which may be sealed with an appropriate plug (not shown) to provide a leak-free seal). Outlet port 611 can be constructed so that a non-zero angle is formed relative to the plane of the major surfaces of top piece 600 to provide gravity-induced settling for any non-adherent cells that might be floating out of the culture chamber, 614, into outlet port 611. The geometry of the hole in the gaskets 613 illustrated in FIG. 6 is circular, but an elliptical or other shaped aperture with the inlet and outlet ports placed in focal points of the shape may be used to provide better fluid distribution (vide infra). Similarly other geometries can be used to allow for the desired shear stress ranges and fluid flow distribution.

In another, simpler configuration only one gasket 602 and no membrane 603 is used. In this embodiment, the enclosure does not comprise separate cell culture and gas chambers and the liquid medium fed into the enclosure via inlet port 610 is charged with the requisite cellular respiratory gases.

The flat bed bioreactors can be assembled in four basic configurations.

Figure 6F:
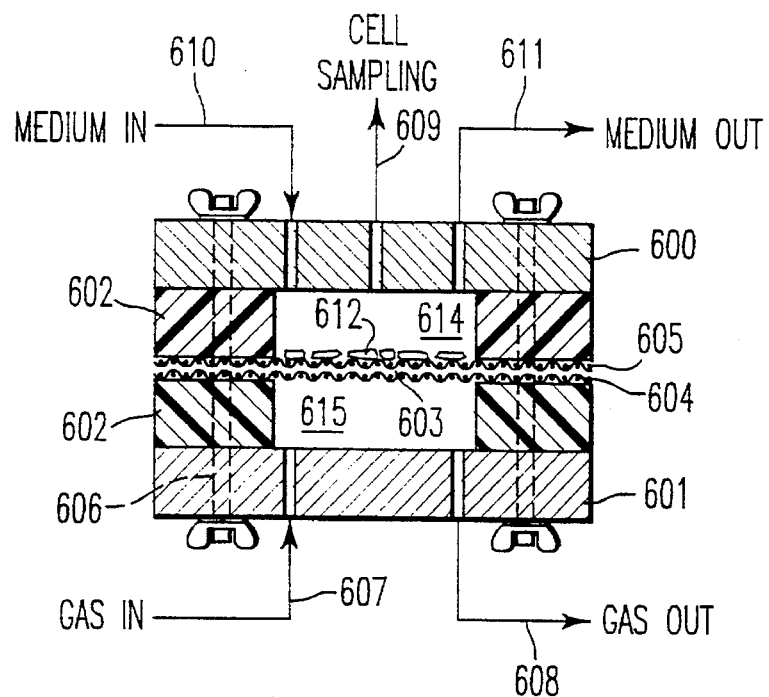
Figure 7A:
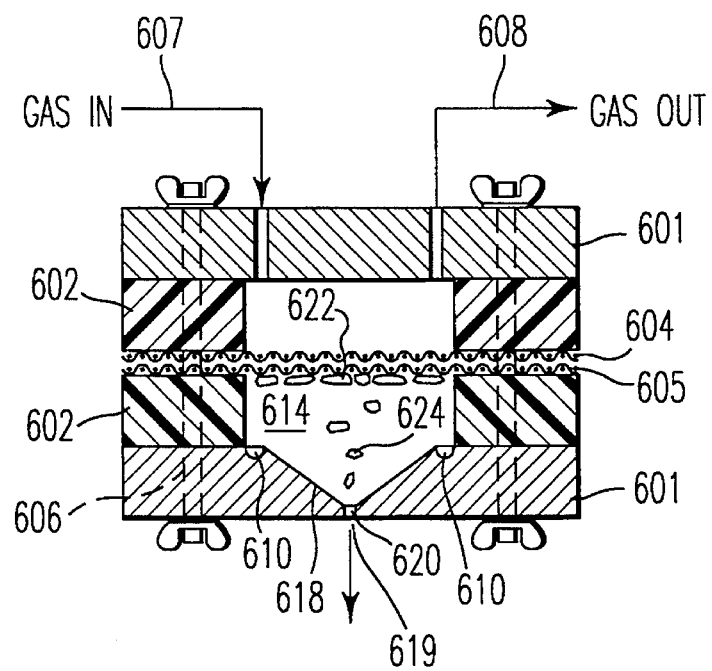
FIGS. 7a and 7b are schematics showing the principal components of the flat-bed hematopoietic bioreactors equipped with a means for continuous or periodic cell harvesting.

Configuration no. 1, which is illustrated in FIG. 6f, provides two compartments; cell culture chamber 614 and gas chamber 615. A double membrane assembly separates the two chambers (for example a ceramic membrane for cell growth/attachment 605 over a hydrophobic gas exchange membrane 604, such as a silicone membrane). In the cell culture chamber 614 liquid medium is perfused in conjunction with liquid medium inlet port 610 and liquid medium outlet port 611, while gas is circulated through the gas chamber 615 in conjunction with gas inlet port 607 and gas outlet port 608. Cells 612 grow in culture chamber 614 on top of ceramic cell attachment/growth membrane 605.

Figure 6G:
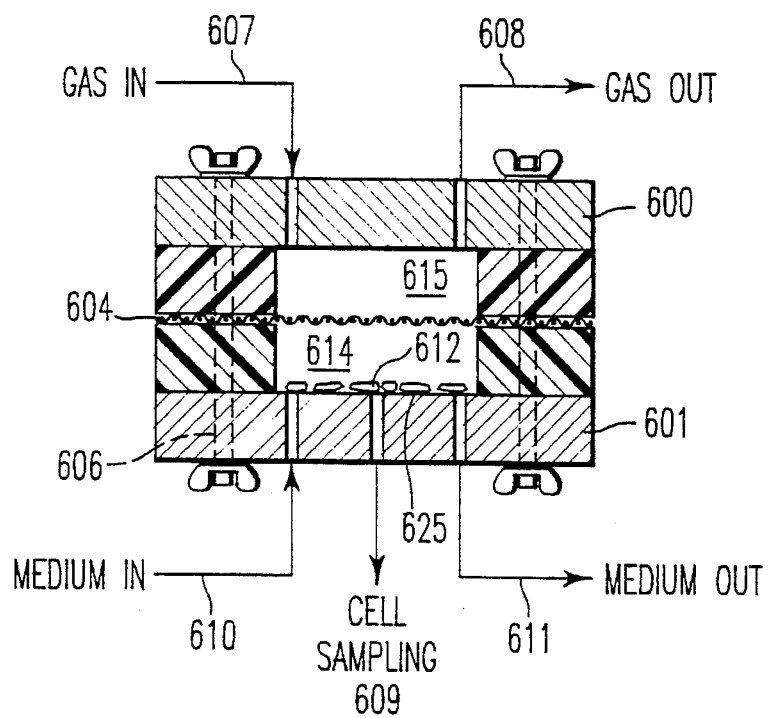

Configuration no. 2, which is illustrated in FIG. 6g, is configuration no. 1 inverted. Here cells 612 grow on surface area 625 of bioreactor bottom 601 at the bottom of culture chamber 614. Preferably surface area 625 is adapted for cell growth/attachment. In this configuration only a single gas exchange membrane 604 and no cell attachment/growth membrane 605 is needed. In this configuration, as with all other configurations, liquid medium is perfused through culture chamber 614 and gas is perfused through gas chamber 615.

Figure 6H:
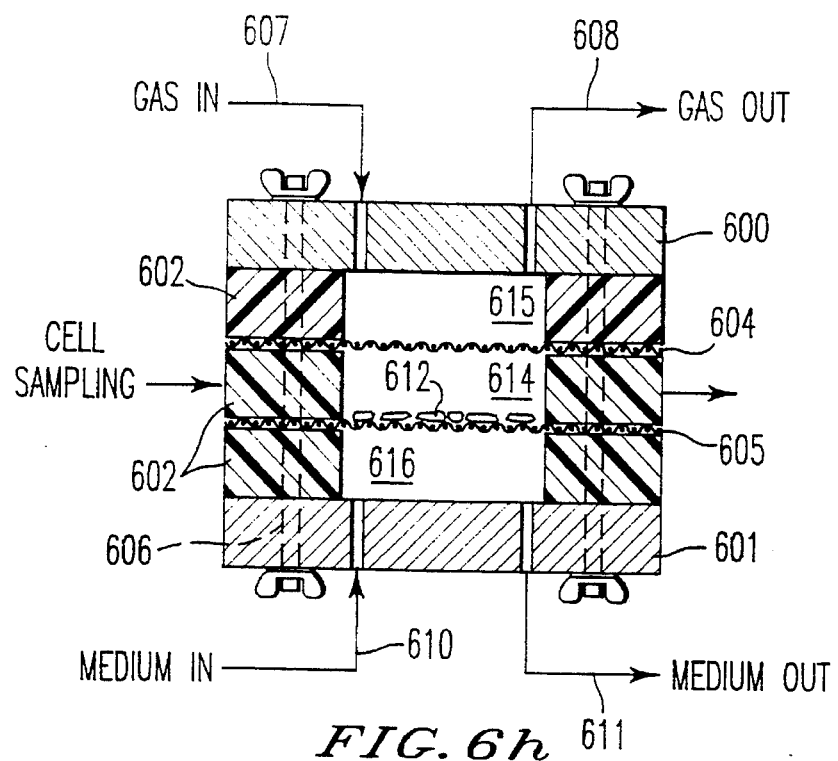

Configuration no. 3, which is illustrated in FIG. 6h is a three-compartment design. Gas is circulated through gas chamber 615 which is situated at the top of the bioreactor and is separated from cell culture chamber 614 by a gas exchange membrane 604. Cells 612 are in cell culture chamber 614 which is separated from liquid medium compartment 616 by a cell growth/attachment membrane 605. In this configuration cell culture chamber 614 is stagnant while liquid medium compartment 616 is continuously perfused with medium via liquid medium inlet and outlet ports 610 and 611.

Figure 6I:
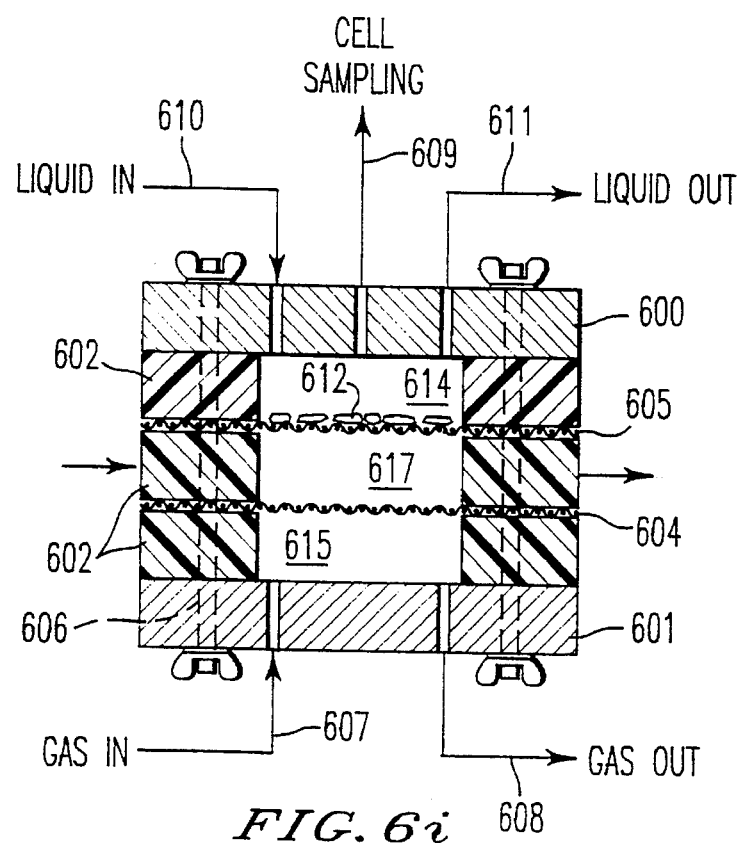

Configuration no. 4 which is illustrated in FIG. 6i is also a three-compartment design. In this embodiment configuration no. 1 is modified by placing a third gasket 602 between the gas exchange membrane 604 and the cell growth/attachment membrane 605. This configuration provides a stagnant liquid medium compartment 617 between gas chamber 615 and the cell bed 612.

To provide for gas mass transfer, cell/extra-cellular matrix attachment, and to prevent water leakage, a two membrane system, illustrated in FIG. 6f, is preferably employed. The lower membrane, 604, is hydrophobic, preventing water leakage, and is permeable to gases. Furthermore, this membrane 604 provides mechanical support for the upper membrane 605. The upper membrane 605 is for cell attachment and/or growth, and may be an inorganic ceramic-based membrane. It can be coated with extra-cellular protein, such as the PepTite-2000 RGD based adhesion protein from Teleos Pharmaceuticals Inc., San Diego. Such proteins are known. See, e.g., Hubbell et al, *Biotechnology* (1991) 9: 568–572. Further, a highly desirable property of the inorganic membrane used is that it becomes transparent upon hydration thus making microscopic observation/monitoring of the cells being cultured possible.

The tubing for providing medium and gases to the bioreactor is connected to the bioreactor top, 600, and bioreactor bottom, 601, using any known suitable fittings, such as polypropylene fittings and Luer Locks rings silicone O-rings which are known to provide good seals and no leakage problems.

This bioreactor and its various configurations meet all the requirements listed above. We now describe, in FIGS. 7a, 7b, 8a and 8b, two configurations that allow for easy and selective on-line harvesting of cells produced in the bioreactor. Any of these two illustrative configurations can be adapted, if desired, to the configurations shown in FIGS. 6a–g and *i*.

I.2. Flat-bed (hematopoietic) bioreactor with single or multiple surfaces and a conical section for cell harvesting (illustrated in FIGS. 7a and 7b).

Figure 7B:
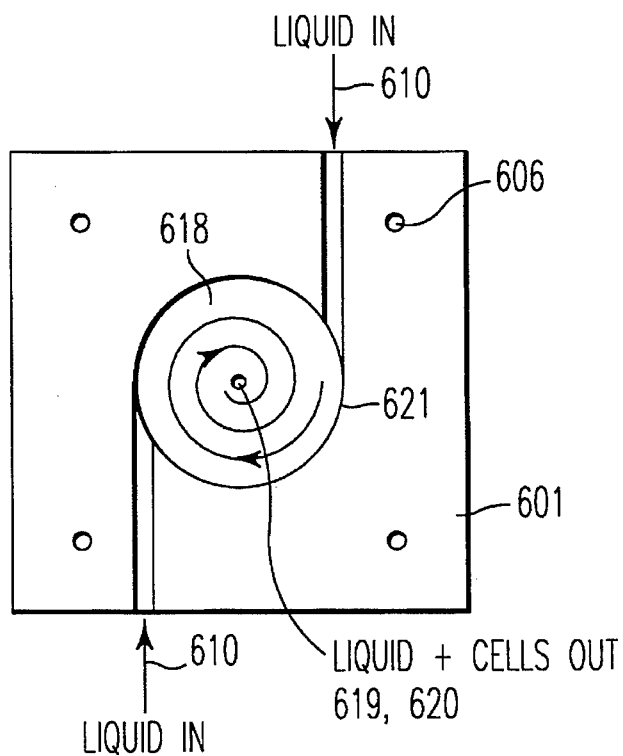

The bioreactor top or bottom forming one of the walls of cell culture chambers 614 in configurations nos. 1 and 4 described above can be configured to allow for continuous, intermittent or periodic harvesting of cells. A shallow cone 618 is created in the bioreactor bottom 601 (or bioreactor top 600, if e.g., the configuration illustrated in FIGS. 6a–e, f, or *i* is used) with a sole liquid medium and harvested cell outlet port 619 situated at the top 620 of the cone 618. In such a configuration, liquid medium outlet ports 611 (not shown) do not have to be used. The liquid medium inlet port(s) 610 are placed at the base 621 of the cone 618, preferably parallel to the outline of the cone as illustrated in FIG. 7b. As the liquid medium is pumped in through the inlet port(s) 610 a circular motion in the liquid medium is induced that spirals towards the top of the cone 620 where the spent liquid culture medium (and non-adherent cells) exit(s) through spent liquid culture medium and harvested cell outlet port 619.

In this configuration non-adherent cells 624 can be harvested continuously, intermittently or periodically through outlet port 619 with adherent cells 622 remaining in the bioreactor. During a cell harvesting operation, or if the cells are harvested continuously, the top of the cone 620 faces downward and the non-adherent cells 624 are swept out of cell culture chamber 614 by the flowing liquid medium 611. If periodic or intermittent cell harvesting is desired the bioreactor is preferably placed such that the cone top 620 faces upward except for the time periods of a cell harvesting operation during which the bioreactor is rotated so that cone top 620 faces downward and the non-adherent cells 624 are collected through outlet port 619.

I.3. Internally inclined hematopoietic bioreactor.

For many applications it may be desired to sample only a selected subset of the entire population of non-adherent cells 624. In particular, harvesting separately the stem and progenitor cells from the more mature cell population is highly desirable for many application. Such separation can be readily accomplished by the use of inclined sedimentation, an illustrative embodiment of which is provided in FIGS. 8a and *b*. This separation, which may be readily adapted to the bioreactor design illustrated in FIGS. 6a–e, f, or *i*, is based on density differences between the various cells in the population of non-adherent cells 624 that are to be separated. Progenitor and stem cells have a lower density than more mature cells such as erythroid and granulocytic cells.

Gravity induced sedimentation can be accomplished in situ in the bioreactors described above by simply placing the bed of adherent cells 622 at a particular angle ($\alpha=15°$ to $75°$, preferably $25°$ to $45°$) relative to horizontal and flowing the liquid medium over the adherent cells 622 in an upward direction. In this case the geometry of the hole 613 in central gaskets 602 may preferably be a rectanguloid as illustrated in FIG. 8b. As illustrated in FIG. 8a, adherent cells 622 may be grown on the cell growth/attachment membrane 605 placed at the top of cell culture chamber 614. Alternatively, the configuration of FIG. 6g may be used, with the major surface 625 of bioreactor bottom 601 which creates the bottom of cell culture chamber 614 modified to provide for cell attachment. The bioreactor is inclined at an angle ($\alpha=15°$ to $75°$, preferably $25°$ to $45°$) from horizontal and liquid inlet port 610 is separated from two outlet ports 611 as illustrated in FIGS. 8a and *b*. Continuous, intermittent of periodic fractionation and harvesting of the non-adherent cell population 624 can thus be accomplished. Using this configuration high density non-adherent cells 623 can be collected from the lower medium outlet port 611 and low density non-adherent cells 629 collected from the upper medium outlet port 611. As also illustrated in FIGS. 8a and *b* the location of lower medium outlet port 611 and medium inlet port 610 can be interchanged and the same cellular separation and harvesting achieved.

FIGS. 11a, b and *c* illustrate another embodiment of the bioreactor of the present invention. In this embodiment, the bioreactor is pivotally mounted on support member 626 via pivot means 627. In this embodiment a single or multiple gas inlet port(s) 607 is used together with multiple gas outlet ports 608, and a plurality of liquid culture medium inlet ports 610 are used in conjunction with a plurality of spent liquid culture medium outlet ports 611. In this embodiment a triangular enclosure—gas chamber and cell culture chamber arrangement—is preferably used, created, as illustrated, through the use of triangularly shaped apertures in gaskets 602.

The bioreactor design illustrated in FIGS. 11a, b and *c* is useful for the continuous harvesting of cells from the bioreactor chamber, with the bioreactor being either in the horizontal or inclined position. As shown in the figure, the liquid culture medium inlet and outlet ports are located on opposite sides of the cell culture chamber with the liquid cell culture medium being situated generally in the center of the cell culture chamber. In this embodiment, the bioreactor may be pivotally mounted on a support means such that the angle of the bioreactor (and hence the angle of the cell bed) can be adjusted as desired. Using this configuration, liquid cell culture medium outlet ports 611 can be tilted upwards allowing efficient cell inoculation and spent medium removal. Subsequently the reactor may then advantageously be placed in a horizontal position thereby permitting the cells to settle on attachment/growth surface 625 for attachment and growth of the stromal and early stem and progenitor cells.

In this configuration, liquid cell culture medium may be (continuously) perfused through the cell culture chamber with the bioreactor being situated horizontally. To harvest non-adherent cells from the bioreactor chamber, the bioreactor can be inclined with liquid cell culture medium outlet ports 611 inclined upward so that density-based cellular separation occurs in the cell culture chamber thereby permitting harvesting of specific cell types.

In another embodiment, the bioreactor may be rotated to a vertical orientation such that liquid culture medium inlet ports 610 are situated at the top and liquid cell culture medium outlet ports 611 are situated at the bottom. Cell culture medium containing the non-adherent stem, progenitor of a mature cells then flow downward and may be removed (continuously) via liquid culture medium outlet ports 611. This configuration may be advantageously used for removal of mature cells that may inhibit hematopoiesis, thereby providing more prolific cultures. Conversely, while in a vertical position, the liquid cell culture medium may flow from ports 610 to 611 with the cells settling at apex 628, which cells may be removed from the cell culture chamber at any desired time by selective removal of spent cell culture liquid medium from the outlet port(s) furthest from apex 628 to the outlet port(s) closest to apex 628.

II. Auxiliary components and overall flowsheet

Figure 9:
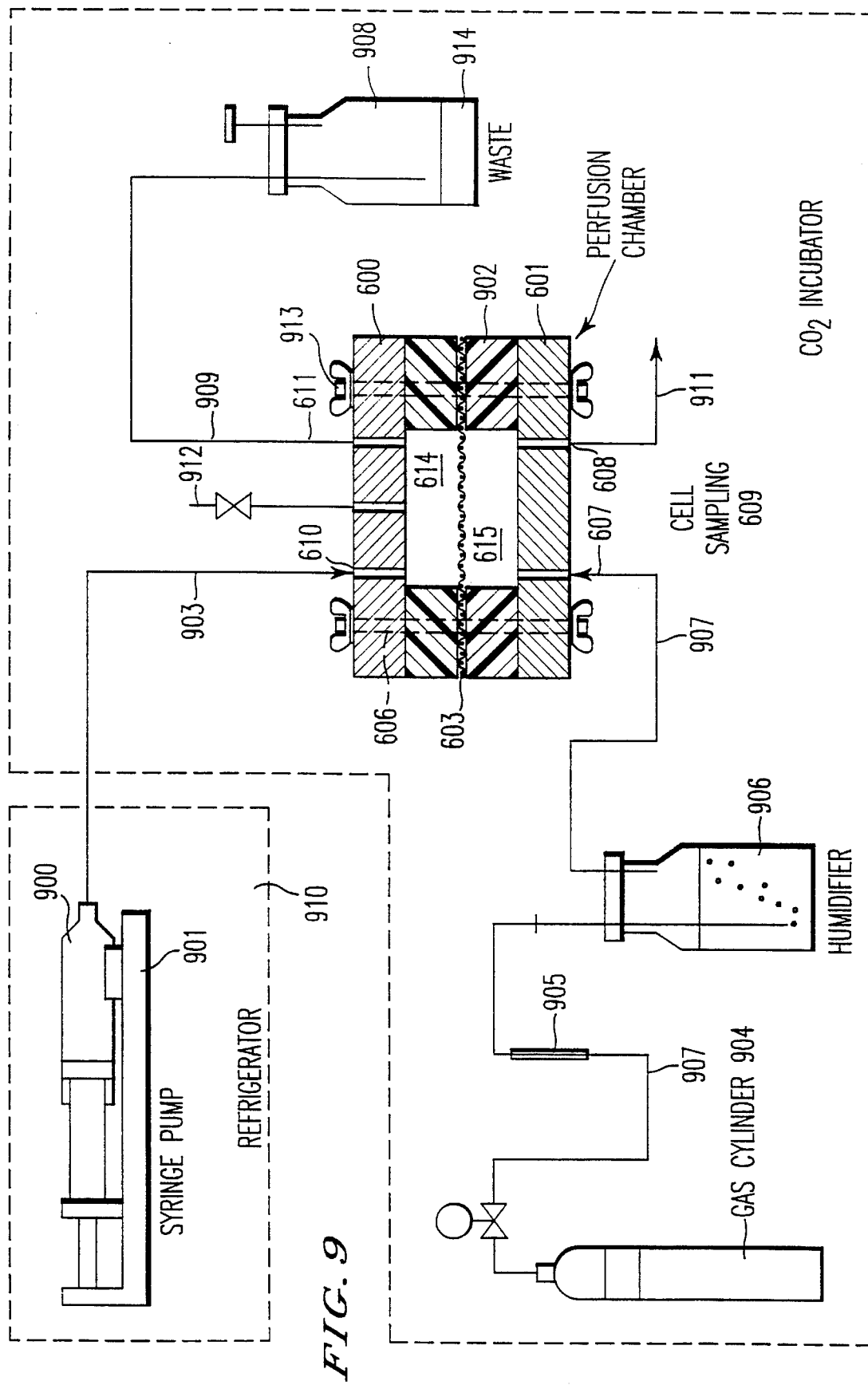
FIG. 9 is an illustration of an automated cell culture system.

A process flow sheet for an illustrative (hematopoietic) bioreactor expansion system is provided in FIG. 9, including the additional components that are required for operation.

Liquid medium 900, which is kept cool (e.g., at about 4° C.) to prevent decay of chemically unstable medium components, such as glutamine and growth factors, is pumped with a pump 901 (e.g., a syringe pump, peristaltic pump, etc.) into cell culture chamber 614 of bioreactor 902 through tubing 903 that preferably is impermeable to water to prevent changes in medium osmolarity prior to entry into cell culture chamber 614. Tubing 903 may have a "slack" so that pump 901 and/or fresh medium reservoir 900 can be moved, e.g., between a cool storage location 910 and a laminar flow hood (not shown) where any desired manipulations can be carried out in a sterile environment. The extra tubing 903 is kept, e.g., in a refrigerator (not shown) so that only a short tube segment is exposed to room temperature or incubator temperature.

Gas is supplied to gas chamber 615 of bioreactor 902 either from a cylinder 904 containing premixed gases (a mixture of 1–50% (v/v), preferably 5–20% (v/v) $O_2$, 5% (v/v) $CO_2$ and the balance $N_2$) or is simply taken from the inside of an incubator (not shown) (typically a mixture of air and 5% (v/v) $CO_2$). The flow rate and composition of the gas stream are thus easily controlled using known methods. The gas may be pumped with a pump (not shown) through a sandstone in a standard cell culture humidifier 906 to give the gas mixture being delivered to gas chamber 615 relative humidities as close to 100% as possible. Gas line 907 can optionally contain a sterile filter 905.

The spent medium may be collected 914 via tubing 909 in a reservoir 908. Samples of spend medium can be advantageously taken from reservoir 908 for analysis of medium components. Spent gas is disposed of via tubing 911, from it may be analyzed using any suitable gas analyzer (not shown). The analysis of the spent liquid medium and/or spent gas may be advantageously used as additional means for monitoring the cell culture. Additionally one may advantageously monitor important culture characteristics, such as pH and dissolved oxygen tension, using means 912.

All the three bioreactors described herein satisfy the criteria enumerated above. Examples of their construction, operation and performance are given below.

Having generally described this invention, a further understanding can be obtained by reference to certain specific examples which are provided herein for purposes of illustration only and are not intended to be limiting unless otherwise specified.

EXPERIMENTAL

I. Formation of Transformants

The growth factor human GM-CSF (Wong, *Science,* (1985) 228 :810–815) was inserted into a eukaryotic expression vector. The HGM-CSF CDNA (EcoRI to AhaIII, approximately 700 bp fragment) was cloned into an EcoRI to PStI fragment of pSP65. (Melton, *Nucl. Acids Res.* (1984) 2: 7035–7056). The resulting plasmid was pSP65GM-CSF. The mouse metallothionein promoter (Glanville, *Nature* (1981) 292: 267–269) was digested with EcoRI and BglII and the approximately 2 kb fragment containing the promoter was inserted into the ECoRI to BamHI fragment of pSP65 to make p65MT. The plasmid pMT GM-CSF was then constructed by digesting pSP65G M-CSF with EcoRI, filling in the overhang with the Klenow fragment of DNA polymerase I and then digesting the resulting linearized DNA with HindIII to isolate the 700 bp fragment comprising the coding region of GM-CSF. This fragment was subcloned into the SalI filled/HindIII site of p65MT. The 2.7 kb fragment comprising the metallothionein promoter and the GM-CSF coding region was then isolated and placed into pSV2neo (Southern and Berg, *J. Mol. Appl. Genet* (1982) 1: 327) from which the SV-40 promoter was removed. This results in the SV-40 poly A signal downstream of the GM-CSF coding sequence.

The neomycin resistant gene, which confers resistance to the antibiotic gentamicin (G418) was taken from pSV2neo by isolating the approximately 3 kb PvuII to EcORI fragment and placing EcoRI linkers onto the PvuII site. The neo resistance gene with EcoRI ends was subcloned into the EcoRI site of the GM-CSF expression plasmid to create the plasmid MTGM-CSFneo.

The plasmid MTGM-CSFneo alone and as a cotransfection with the plasmid (Yang, *Cell* (1986) 47: 3–10) encoding the gibbon ape IL-3 gene under the control of the SV-40 promoter and poly A site, were transfected by electropotation of linearized DNA into the African green monkey cell line CV1 and the mouse cell line NIH 3T3 cells. Transformants were selected by selection in media containing 500 mg/ml of G418, isolated, and screened for production of GM-CSF or IL-3 by bioassay of supernatants using AML-193 cells (Adams et al., *Leukemia* (1989) 3: 314). Several of the positive lines were then employed as stroma for human bone marrow cells in Dexter culture.

In addition, normal mouse bone marrow cells were transfected with the above plasmid using the calcium/phosphate method of Okayama (Chen, *Mol. Cell. Biol.* (1987) 7: 2745–2752) and were found to efficiently express the introduced genes.

GM-CSF and IL-3 secretion by the transfected fibroblants was investigated. Serum free 72 hour culture supernatants were obtained from the NIH-3T3 cells and assayed for hGF secretion by 3 H uptake on target cells inhibitable by neutralizing rabbit anti-GM-CSF or anti-IL-3 antibodies. Proliferation induced by 20 mq/ml GM-CSF was set as 100 units GM-CSF and that induced by 10 ng/ml IL-3 was set as 100 units IL-3. The co-transfected cells produced about 35 units/ml of GMCSF and about 57 units/ml of IL-3.

II. Perfusion Chamber

The perfusion chamber is a glass cylinder with Delrin caps to allow for autoclaving without deformation and biocompatability. The caps have cylindrical groves into which the glass cylinder fits. At the bottom of the grove an O-ring is placed to seal the lumen of the chamber. The caps have several holes into which Luer (Luer Lok) fittings are provided into which media and gas delivery lines are put as well as an extended tube into the central section of the chamber to sample adherent and/or non-adherent cells. The caps are attached with three long bolts, spaced 120°, placed outside the glass cylinder; wing nuts and washers are used to tighten the assembly.

The chamber is hooked to a side reservoir. The loop contains a pump, a chamber of on-line sensors, oxygenator, and sample and injection ports in addition to the side media reservoir. The media in the side reservoir is then slowly exchanged using a separate pump. This configuration allows for separate control of the media exchange rate and the flow rate through the oxygenator and perfusion chamber. The former is used to control the longer term change in the media composition and perfusion, while the latter may be used to control the dissolved oxygen tension and flow patterns in the chamber. The use of a small mesh polysulfonate membrane allows for plug flow in the chamber and the precise control of delivery of growth factors and other special compounds which one may wish to introduce into the bioreactor in very precise amounts.

The transfected stromal cells are seeded either over a bed of shredded collagen sponge or the stromal cells are placed on one side of a 5μ porous polycarbonate filter precoated with collagen and the stromal cells allowed to adhere to the filter over a number of hours. The cells are allowed to grow in an appropriate nutrient medium until the cells become confluent on one side while sending cytoplasmic projections through the pores. Bone marrow cells are then seeded on the other side of the membrane and the stem cells attach to the intruded cytoplasmic projections which have passed through the pores.

After autoclaving the chamber and components of the loop, the reactor is assembled in a sterile environment. The media is then circulated through the side loop and chamber for a few days while signs of contamination are monitored. The central section of the bioreactor in then inoculated with either the extracellular matrix alone or a preinoculated extracellular matrix support that contains the stromal cells. The stromal cells may then be kept in the chamber for a period of a few days while their metabolic performance and/or growth factor responsiveness is monitored and if results are satisfactory, the bone marrow is inoculated or immediately seeded with bone marrow. In either case, the cell layer in kept at the bottom of the central section of the perfusion chamber.

The cells lay down additional extra-cellular matrix and the cell layer adheres to the support. Where the membrane is used, the chamber may be inverted and the cell layer in then located at the ceiling of the central section. In this configuration, the maturing cells settle on the bottom of the central chamber as they loose their adherence to the stromal layer. The non-adherent cells are then harvested by constant cell flow, driven by the medium perfusion pressure, into the exit tubing.

In a typical run, the chamber was inoculated with NIH-3T3 cells on day one on shredded collagen sponge support. For the first 40 days perfusion rates and other operating variables were adjusted. At day 40 a reasonable steady state was achieved which was maintained for about 20 days. On day 64 the chamber was seeded with $33 \times 10^6$ human bone marrow cells. For the first 10 days the harvested cell count decreased until it settled in a steady state of about $7-8 \times 10^5$ cells produced every three days. Flow cytometric analysis showed that a constant fraction, about 20% of the harvested cells were HLA-DR positive. On day 90 a pump failure was experienced and the pH dropped below 6.9 overnight. When the perfusion rate was restored the production of non-adherent cells recovered and was approaching the previous steady state production rate when a bacterial contamination occurred. At this point, the study was terminated.

The above results demonstrated that a perfusion chamber is capable of performing ex vivo hematopoiesis, hematopoiesis may be restored ex vivo after a pH drop, the glucose concentration data showed that the hematopoietic cells grow primarily aerobically on glucose, since the glucose concentration drops after inoculation without increasing the lactate concentration indicating that oxygenation is limiting. The glucose/lactate (anaerobic) metabolism appears to be primarily due to the NIH-3T3 stromal bed. Similarly, the glutamine and ammonia concentrations reach preinoculus levels once the hematopoietic cell number levels off, implying that the glutamine consumption by the bone marrow cells is much less than that of the stromal bed.

III. Monitoring of Metabolic Products

The consumption and formation rates of glucose and lactate as well as glutamine and ammonia were determined for transfected NIH-3T3 cells. (The medium was IMDM plus 20% FCS). Increased glucose consumption was only observed for daily fed T-flasks, whereas all less frequently fed cultures follow the same slowly diminishing glucose uptake rate pattern. Cultures that were exchanged 50% daily were switched to the 100% daily exchange schedule on day 18, which resulted in an immediate increase in glucose consumption following the same trend as that observed for cultures exchanged 100% daily from day one. Lactate production rates follow a similar pattern, as the lactate yield on glucose is essentially a constant (0.9 lactate/glucose; indicating a largely anaerobic stromal metabolism).

The glutamine and ammonia concentrations show a pattern analogous to the glucose/lactate metabolism. Using values corrected for chemical decomposition of glutamine at 37° C., the glutamine consumption rate versus the glucose consumption rate shows relative uptake rates are constant, about 1:8 glutamine: glucose. The predicted optimum ratio varies with oxygen uptake rate the ratio drops with increasing optimum uptake rate.

Analogous conclusions were supported by glucose/lactate metabolic data derived from normal bone marrow stromal fibroblants. Under conditions of infrequent medium exchange the cultures were primarily anaerobic, with high steady state levels of lactate rapidly achieved and maintained. With more frequent medium exchanges, the cell metabolism became more rapid, with increased glucose consumption and lactate production. No detectable consumption of glutamine was observed after correcting the data for spontaneous chemical decomposition. For both 3T3 cells and normal human bone marrow cells, the cells continue to divide and crowd when the serum/media exchange rate was above what appears to be a critical replacement schedule.

To further ascertain the relative importance of perfusion rate of serum versus that of nutrients, the following experiments were performed: (1) one set of T-flasks with 20% serum containing media exchanged daily; (2) two sets of T-flasks, one with 20% serum and the media exchanged every other day and one with 10% serum with the media exchanged daily; (3) two sets of T-flasks, one with 10% serum and the media exchanged every other day, one with 5% serum with the media exchanged daily; (4) two sets of T-flasks, one with 5% serum and the media exchanged every other day and one with 2.5% serum with the media exchanged daily. The serum exchange rate is the same within each group while the exchange rate of the nutrient containing media varies. The results from these experiments show that it is the exchange rate of the serum that is critical.

While for the experiment 1) glucose consumption increased and by day four had substantially flattened out to a rate of about 9.5 mmoles/per day, in all of the other cases, the glucose consumption started below the original glucose consumption of Group I and dropped off in a substantially linear manner regardless of whether twice the amount of serum was used and changed every other day or half the amount of serum was used and the media changed every day. This supports the need for a critical perfusion rate of serum or one or more serum components that influence the metabolic growth behavior of the stromal cells.

It in evident from the above results, that one may grow hematopoietic cells in a bioreactor in an efficient manner. Stromal cells can be provided from homologous or heterologous sources, where the stromal cells have been transfected with genes to provide for the important growth factors. In this manner, serum need not be added to the media to support the growth of the cells. By providing for stromal cells which adhere to a support in a manner which allows for separation of hematopoietic cells from the stromal cells, the hematopoietic cells may be continuously harvested for use. By appropriate choice of combinations of growth factors, specific lineages of hematopoietic cells may be grown. In addition, if desired, the stromal cells may provide for a reservoir of transfecting viruses for the introduction of genes into the hematopoietic cells.

Example 1

We will now describe a specific embodiment of the flat-bed membrane bioreactor (see I.1 above) and its function in an overall system.

Operating Procedures

A. Starting up the perfusion chambers

Cells. The cells are treated prior to inoculation in the same fashion as they are prepared for Dexter cultures. After aspiration from a donor mononuclear cells are separated on a discontinuous density gradient (Ficoll-Paque) and then washed several times in the culture medium. If an enriched inoculum is desired, then at this stage procedures to enrich for progenitor and stem cells are invoked. This procedure typically takes about half a day.

Medium. The medium used is the standard Dexter medium, 10% horse serum, 10% fetal calf serum, $10^{-5}$M hydrocortisone and IMDM. In addition hematopoietic growth factors, such as Il-3, GM-CSF and Epo are used, as previously described (Schwartz et al 1991), and c-kit ligand.

Perfusion Chambers. The preparation of the perfusion chambers starts one day prior to inoculation. Assembly of a set of 6–10 perfusion takes about 6 to 8 hours. This involves sizing/cutting tubing, putting fittings into the chamber, preparing the medium bottles, etc. At the end of the day the full chamber assembly (less the tubing and attachments for the gas exchange) is autoclaved without medium (all components are autoclavable). The set of chambers may then be stored in a sterile culture hood. At a later time, the full set of components is assembled in the hood, the medium introduced, the membrane coating applied (e.g., PepTite 2000), cells inoculated, the chambers placed in the incubator, the syringes loaded into the pump and stored in the refrigerator. The chamber preparation, cell handling, and inoculation typically takes two full days. The perfusion typically begins after the cells have settled in the chamber for 12 to 24 hours.

Membranes. In this example we used either a silicone membrane (specification) or a Teflon® membrane (of 0.001 inch thickness) as gas exchange membranes. For cell growth and attachment we used a ceramic membrane (AnoTec® 0.02 micron, nontreated).

B. Running the perfusion chambers.

Replacing Syringes. Syringe pumps were used for this example. The syringes are replaced on a fixed schedule. For instance during the initial runs with the chambers 10 ml syringes were used at a flow rate of 2 mls per day. Syringes thus were replaced ever 5th day. The syringe pump is moved from the refrigerator to the hood where the syringes are replaced in a sterile environment. This transfer of the pump is allowed by the "slack" in the medium inlet line as described above.

Microscopic observation. The top and bottom of the perfusion chamber and the gas exchange membrane are transparent. The inorganic membrane becomes transparent once it is hydrated and thus during operation one can observe the cells in the chamber through a microscope. To do so one needs a long distance objective.

Sampling cells. Two methods were used for periodic cell sampling. Firstly, we let cells settle by gravity inversion for two hours and then we replace 2 mls in the chamber by pushing liquid through the inlet port and collecting it from the outlet line. Secondly, we have pulled directly through the sampling port 2 mls leaving air space in the chamber that then disappears within a day due to the incoming medium. The second method is more invasive and yields a higher number of cells (approximately four-fold). The cell sampling takes place in a laminar flow hood. The set of chambers is moved from the incubator to the hood; the length of the inlet medium line should allow for this transfer. The adherent cells can be removed in a similar fashion after treatment with trypsinization.

C. Performance.

We will now describe the results from several tests of these biorectors. Multiple copies of a small bioreactors, specific dimensions described in FIGS. 6a–i, were operated simultaneously under various conditions.

Example 2

Growth of Human Bone Marrow in Bioreactors at Different Oxygenation Rates

Sets of hematopoietic bioreactors have been run successfully repeatedly.

We include data here on the operation of a set of chambers, of dimension indicated in FIGS. 6a–e at different oxygen rates.

Bioreactor preparation.

Configuration. 2-chamber design, i.e., $O_2$ on top compartment/medium flow in the bottom. The cells were grown on polycarbonate surface which is the bottom wall of the reactor. Across the bottom cell compartment, a medium was supplied and withdrawn by syringe needles inserted through a silicone gasket (medical grade).

Oxygenation membranes. The two compartments were separated by a gas permeable membrane for oxygenation. To optimize oxygenation rate to a cell layer on the polycarbonate surface, three membranes were tested: teflon 100 (0.001 inch in thickness), silicone 1500 (0.015 inch), and silicone 3000 (0.03 inch). The two silicone membranes were medical grade and reinforced with a dacron net.

Dimensions. The depth of the cell growth chamber was 3 mm, while that for gas flow was 1.5 mm. The diameter of all chambers was around 30 mm.

Sterilization. The reactors were assembled without tightening the bolts and autoclaved for 30 minutes at liquid cycle. After cooling and drying in a laminar flow hood overnight, all screws and fittings were tightened. The reactors were rinsed with 10 ml of Hanks balanced salts solution (HBSS) before medium was introduced.

Medium.

In DEXTER medium Growth factors were added to the standard Dexter medium (i.e., 10% v/v) fetal calf serum, 10% horse serum plus 80% medium, in this case Iscove's Modified Dulbecc's Medium) in the following concentrations: IL-3 (5 units/ml), GM-CSF (5 ng/ml), Epo (0.1 units/mL) and MGF (10 ng/ml).

Bioreactor operation.

Bioreactors with different gas permeable membranes as described above were operated under different oxygen concentrations in the gas compartment. Levels of oxygen tested were 5% (also contains 5% $CO_2$, and balanced with $N_2$) and 20% (air containing 5% $CO_2$). The both gases were saturated with a sterilized water before introduction to the bioreactors. Each condition was operated in triplicate (see Table 1 below). Each reactor was inoculated with 7.0 million cells purified by a standard Ficoll procedure. Medium perfusion rate was 0.75 ml/day, and cell culture temperature was 37° C. in a warm room.

TABLE 1

Bioreactor arrangement:

| | | Oxygen level | |
|---|---|---|---|
| | | 5% | 20% |
| Gas premeable membrane | Teflon 100 (0.001 inch thick) | — | #27, #28, #29 (1X)† |
| | Silicone 1500 (0.015 inch thick) | #21, #22, #23 (6X) | #30, #31, #32 (25X) |
| | Silicone 3000 (0.03 inch thick) | #24, #25, #26 (3X) | #33, #34, #36 (15X) |

†Approximate indicator of relative oxygen transfer rate to the rate across teflon membrane under 20% oxygen. The numbers indicated designate a particular bioreactor unit.

Sampling. One week sampling schedule was used. For the first week, non-adherent cells were sampled in a volume of 0.6 to 0.8 ml. At the end of incubation for two weeks, non-adherent cells were harvested by collecting medium and by washing with HBSS three times (total 8 to 11 ml). Adherent cells were trypsinized at room temperature for 15 to 20 minutes. All cell samples was plated for progenitor cell assay on methyl cellulose at densities of $2.5 \times 10^4$ cells/ml for the first week samples and $1 \times 10^5$ for the second week samples.

Results.

Figure 10A:
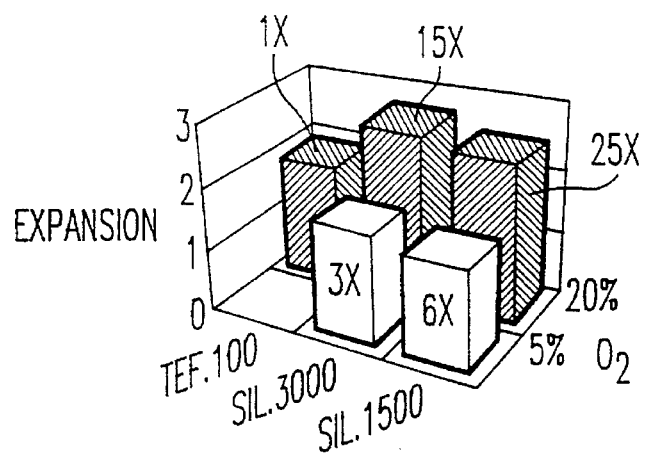
FIGS. 10a–10c illustrate total cell, GM and BFU expansion, respectively, as a function of (i) gas membrane type and (ii) $O_2$ concentration.
Figure 10B:
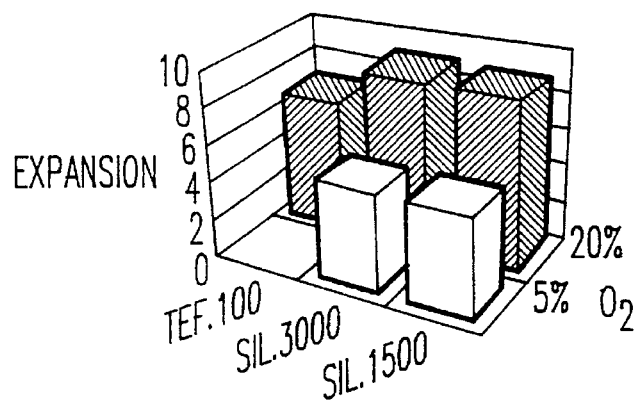
Figure 10C:
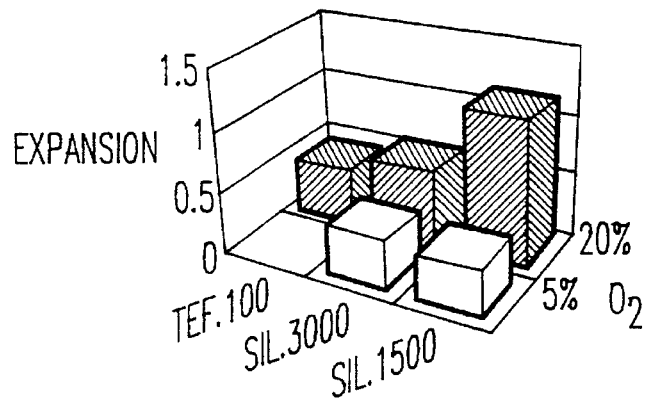

The results are tabulated (Table 2 and shown graphically in FIGS. 10a–c) as expansions in 1) total cells, 2) Granulocyte-macrophage progenitors (GM-CFU) and 3) Erythroid burst forming units (BFU). The expansion is defined as the cumulative production relative to the inoculum. Operations of the adherent cell layer were as follows:

1. Cell surface coverage. For the first week culture, cells covered more than 40 to 50% of the surface in all reactors. A highest coverage was found in reactors under 20% $O_2$ and with silicone 1500. At the end of the second week of operation, the cell bed in the reactors with silicone 3000 membrane appeared the healthiest. Under most conditions, the coverage was lower at the center of reactors than at the periphery.

2. Stromal cells. Attachment of fibroblast had been observed at a low cell density region on the polycarbonate surface before non-adherent cells got confluent. The stromal cell layer was not totally confluent after two weeks, but was so in certain regions.

Conclusions.

The chambers support the expansion of human bone marrow cells. Performance improved by increased oxygen availability. Best results were obtained at 20% oxygen with either of the two silicone membranes. Under these conditions the total cell number increased almost by a factor of 3. The density of GM-CFU increased in the total cell population by a factor of approximately 3 leading to an almost 9-fold expansion in GM-CFUs.

Example 3

Ten-Fold Scale-Up

The above results were repeated in unit with a 10-fold larger area for cell attachment. Vertical dimensions were kept as in Example 2. The fluid flow pattern was altered slightly. The inlet was through the center port and three ports were installed on the periphery spaced 120 degrees apart. These three ports were used for the outflow of medium.

The cell production data is shown in Table 3. The chamber was inoculated with 35 million cells and the cumulative cell production was 300 million cells, or a 8.6-fold expansion in total cell number. As in EXAMPLE 1 an enrichment in GM-CFU progenitor cell density was observed leading to a better than 31-fold expansion. The total number of GM-CFU produced was over 2 million. A typical transplant carries about 10 million GM-CFU. Thus, the bioreactors described by the inventors can produce a clinically meaningful number of hematopoietic progenitor cell from a single aspirate.

TABLE 2

| | | | Expansion | | |
|---|---|---|---|---|---|
| Specification #1 Oxygen tension | Specification #2 Gas membrane | Chamber | total cell | GM | BFU |
| 5% | Silicone 1500, 0.015" thick (6X)† | #21 #22 #23 | 1.52 1.73 1.52 | 4.98 5.90 5.16 | 0.27 0.62 0.18 |
| | | avg. st. dev. | 1.59 0.12 | 5.35 0.49 | 0.36 0.23 |
| 5% | Silicone 3000, 0.030" thick (3X) | #24 #25 #26 | 1.59 1.82 1.85 | 5.27 5.54 4.63 | 0.27 0.44 0.48 |
| | | avg. st. dev. | 1.76 0.14 | 5.15 0.47 | 0.40 0.11 |
| 20% | Teflon 100, 0.001" thick (1X) | #27 #28 #29 | 1.60 2.25 1.94 | 5.23 7.43 8.09 | 0.29 0.68 0.30 |
| | | avg. st. dev. | 1.93 0.32 | 6.92 1.50 | 0.42 0.22 |
| 20% | Silicone 1500, 0.015" thick (25X) | #30 #31 #32 | 2.64 2.60 2.24 | 9.11 9.05 8.16 | 0.51 1.84 1.05 |
| | | avg. st. dev. | 2.49 0.22 | 8.77 0.54 | 1.13 0.67 |
| 20% | Silicone 3000, 0.030" thick (15X) | #33 #34 #36 | 2.17 3.00 2.93 | 7.46 9.50 9.91 | 0.60 0.37 0.67 |
| | | avg. st. dev. | 2.70 0.46 | 8.95 1.31 | 0.55 0.16 |

†Theoretical indicator for oxygen transfer rate based on the rate across teflon under 20% oxygen.

TABLE 3

No. of cells inoculated 3.50E+07
Growth factors IL-3 (5 U/ml) + GM-CSF (5 ng/ml) + Epo (0.1 U/ml) + MGF (10 ng/ml)
Medium Perfusion Rate 7.2 = 8.6 ml/day

| Day | | # Cells Removed (inoculated) | #CFU-GM per 1e5 | #BFU-E per 1e5 | Total # of CFU-GM Removed | Total # of BFU-E Removed | Expansion of CFU-GM | Expansion of BFU-E |
|---|---|---|---|---|---|---|---|---|
| 0 | inoculum | −3.50E+07 | −193.5 | −505.5 | −6.77E+04 | −1.77E+05 | | |
| 7 | NA cells | 7.54E+07 | 642 | 250 | 4.84E+05 | 1.89E+05 | 7.15 | 1.07 |
| 14 | NA cells | 1.76E+08 | 762 | 56 | 1.34E+06 | 9.86E+04 | 19.85 | 0.56 |
| 14 | Wash 1 cells | 8.40E+06 | 658 | 46 | 5.53E+04 | 3.86E+03 | 0.82 | 0.02 |
| 14 | Wash 2 cells | 4.30E+06 | 852 | 36 | 3.66E+04 | 1.55E+03 | 0.54 | 0.01 |
| 14 | Wash 3 cells | 3.12E+06 | 594 | 32 | 1.85E+04 | 9.98E+02 | 0.27 | 0.01 |
| 14 | Adh cells | 3.96E+06 | 336 | 20 | 1.33E+04 | 7.92E+02 | 0.20 | 0.00 |
| 14 | Wash bottle | 2.88E+07 | 556 | 40 | 1.60E+05 | 1.15E+04 | 2.36 | 0.07 |
| 14 | subtotal | 2.25E+08 | | | 1.63E+06 | 1.17E+05 | 24.05 | 0.66 |
| 14 | Total | 3.00E+08 | | | 2.11E+06 | 3.06E+05 | 31.19 | 1.73 |

All publications and patent applications cited in this specification are herein incorporated by reference as if each individual publication or patent application were specifically and individually indicated to be incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A bioreactor suitable for culturing human stem cells or human hematopoietic cells, comprising:

an enclosure defining a cell culture chamber in which human stem cells or human hematopoietic cells may be introduced and cultured, said enclosure having substantially the shape of at least a sector of a circle;

means for perfusing a liquid cell culture medium through said cell culture chamber; and means in said enclosure for contacting liquid cell culture medium being perfused through said cell culture chamber with a source of oxygen so that the liquid cell culture medium being perfused through said cell culture chamber is oxygenated, wherein said cell culture medium perfusing means includes at least one radially inward located culture medium inlet and at least one radially outward located outlet, so that a radial culture medium flow path is formed between said at least one inlet and said at least one outlet.

2. The bioreactor of claim 1 wherein said means for contacting liquid cell culture medium with a source of oxygen comprises a gas permeable membrane separating the liquid cell culture medium in said enclosure from a source of oxygen.

3. The bioreactor of claim 2 wherein said membrane maintains a depth of said cell culture chamber at approximately 3 mm.

4. A bioreactor suitable for culturing human stem cells or human hematopoietic cells, comprising:

an enclosure defining a cell culture chamber in which human stem cells or human hematopoietic cells may be introduced and cultured;

means for perfusing a liquid cell culture medium through said cell culture chamber, said culture medium perfusing means including at least one culture medium inlet and at least one outlet so that a culture medium flow path is formed between said at least one inlet and said at least one outlet, said cell culture chamber being shaped to create a substantially radial flow of cell culture medium through said flow path; and means in said enclosure for contacting liquid cell culture medium being perfused through said cell culture chamber with a source of oxygen so that the liquid cell culture medium being perfused through said cell culture chamber is oxygenated.

5. The bioreactor of claim 4, wherein said enclosure defining a cell culture chamber comprises a surface area suitable for cell attachment.

6. The bioreactor of claim 5, wherein said surface area suitable for cell attachment is a bioactive surface for specific cell attachment.

7. The bioreactor of claim 5 wherein said surface area suitable for cell attachment comprises a surface area suitable for attachment of a stromal layer in said cell culture chamber and wherein said flow path is comprised by a portion of said cell culture chamber substantially unobstructed by said stromal layer and through which said cell culture medium may freely flow.

8. The bioreactor of claim 4 wherein said flow path is comprised by a portion of said cell culture chamber through which said cell culture medium can freely flow.

9. The bioreactor of claim 4 wherein said means for contacting liquid cell culture medium with a source of oxygen comprises a gas permeable membrane separating the liquid cell culture medium in said enclosure from a source of oxygen.

10. The bioreactor of claim 9 wherein said membrane maintains a depth of said cell culture chamber at approximately 3 mm.

* * * * *